United States Patent
Nelson et al.

(10) Patent No.: US 10,828,204 B2
(45) Date of Patent: Nov. 10, 2020

(54) APPARATUS AND METHOD FOR FORMING ABSORBENT CORES

(75) Inventors: Chris Nelson, Plymouth, WI (US); Collin Heinz, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 13/607,127

(22) Filed: Sep. 7, 2012

(65) Prior Publication Data

US 2013/0240125 A1 Sep. 19, 2013

Related U.S. Application Data

(60) Provisional application No. 61/532,418, filed on Sep. 8, 2011.

(51) Int. Cl.
*A61F 13/15* (2006.01)

(52) U.S. Cl.
CPC .. *A61F 13/15699* (2013.01); *A61F 13/15764* (2013.01)

(58) Field of Classification Search
CPC .......... A61F 13/15634; A61F 13/15674; A61F 13/15658; A61F 2013/530562; A61F 13/15764; A61F 13/15699
USPC ................................. 493/418, 359
See application file for complete search history.

(56) References Cited

U.S. PATENT DOCUMENTS

| 5,762,844 A * | 6/1998 | Van Himbergen ......................... A61F 13/15617 264/112 |
| 6,080,909 A * | 6/2000 | Osterdahl et al. ............ 604/368 |
| 6,093,474 A * | 7/2000 | Sironi ................. A61F 13/1565 156/169 |
| 6,652,798 B1 | 11/2003 | Edvardsson |
| 6,811,642 B2 * | 11/2004 | Ochi ............................ 156/213 |
| 7,048,725 B2 * | 5/2006 | Kling et al. ............. 604/385.01 |
| 7,204,682 B2 * | 4/2007 | Venturino et al. ........... 425/82.1 |
| 8,178,035 B2 * | 5/2012 | Edvardsson et al. ......... 264/517 |
| 8,182,735 B2 * | 5/2012 | Edvardsson .................. 264/517 |
| 8,182,736 B2 * | 5/2012 | Edvardsson .................. 264/517 |
| 8,206,533 B2 | 6/2012 | Hundorf et al. |
| 2003/0150551 A1 | 8/2003 | Baker |
| 2004/0061264 A1* | 4/2004 | Heyn et al. ................... 264/518 |

(Continued)

FOREIGN PATENT DOCUMENTS

| EP | 0589859 A1 | 3/1994 |
| EP | 0796072 B1 | 6/1999 |

(Continued)

OTHER PUBLICATIONS

International Search Report dated Jun. 3, 2013 regarding EP Application No. 12183745.4, 5 pages.

(Continued)

*Primary Examiner* — Vishal I Patel
(74) *Attorney, Agent, or Firm* — Ziolkowski Patent Solutions Group, SC

(57) ABSTRACT

Several variations of core formation techniques and machines to produced cores are disclosed, including a large and small discrete core, formed on a screen and combined; a large and small continuous core, formed on a web; and two and three-dimensional cores, formed on a screen, and core formation on a non-woven web.

19 Claims, 31 Drawing Sheets

(56) References Cited

U.S. PATENT DOCUMENTS

| | | | |
|---|---|---|---|
| 2007/0027435 A1* | 2/2007 | Nakagawa | A61F 13/15203 604/368 |
| 2008/0312625 A1 | 12/2008 | Hundorf et al. | |
| 2009/0212468 A1* | 8/2009 | Edvardsson et al. | 264/511 |
| 2010/0001426 A1 | 1/2010 | Edvardsson | |
| 2010/0249737 A1* | 9/2010 | Ito et al. | 604/367 |
| 2012/0270715 A1* | 10/2012 | Motegi et al. | 493/374 |
| 2012/0312463 A1* | 12/2012 | Ogasawara et al. | 156/245 |

FOREIGN PATENT DOCUMENTS

| | | |
|---|---|---|
| EP | 1922043 B1 | 10/2009 |
| EP | 2043576 B1 | 10/2012 |
| EP | 2273959 B1 | 12/2013 |
| EP | 1974705 B1 | 3/2014 |
| WO | WO 2006/074073 A1 | 7/2006 |
| WO | WO 2007/014235 A1 | 2/2007 |
| WO | WO 2010/101278 A1 | 9/2010 |

OTHER PUBLICATIONS

Notice of Opposition to a European Patent, relating to EP Patent No. EP2609899, dated Jul. 22, 2015, 15 pages.
General Disposables Machinery Invoice No. 00000829/V1, dated Oct. 12, 2004, 9 pages.
General Disposables Machinery Invoice No. 00000909/V1, dated Oct. 12, 2004, 6 pages
General Disposables Machinery Invoice No. 00000648/V1, dated Jul. 30, 2009, 12 pages.
GDM Operating and Maintenance Manual "Production of Adult Diaper Machine AT 450 NEOS 3 Flex Adult", Manual No. D0000511, dated Jul. 23, 2009, 64 pages.
Proceedings pertaining to EP Patent Application No. 12183745.4, 546 pages, dated Mar. 21, 2017.
Opposition proceedings relating to EP2609899, dated Aug. 2, 2017, 320 pages.
Opposition proceedings relating to EP2694006, dated Jul. 13, 2017, 358 pages.

\* cited by examiner

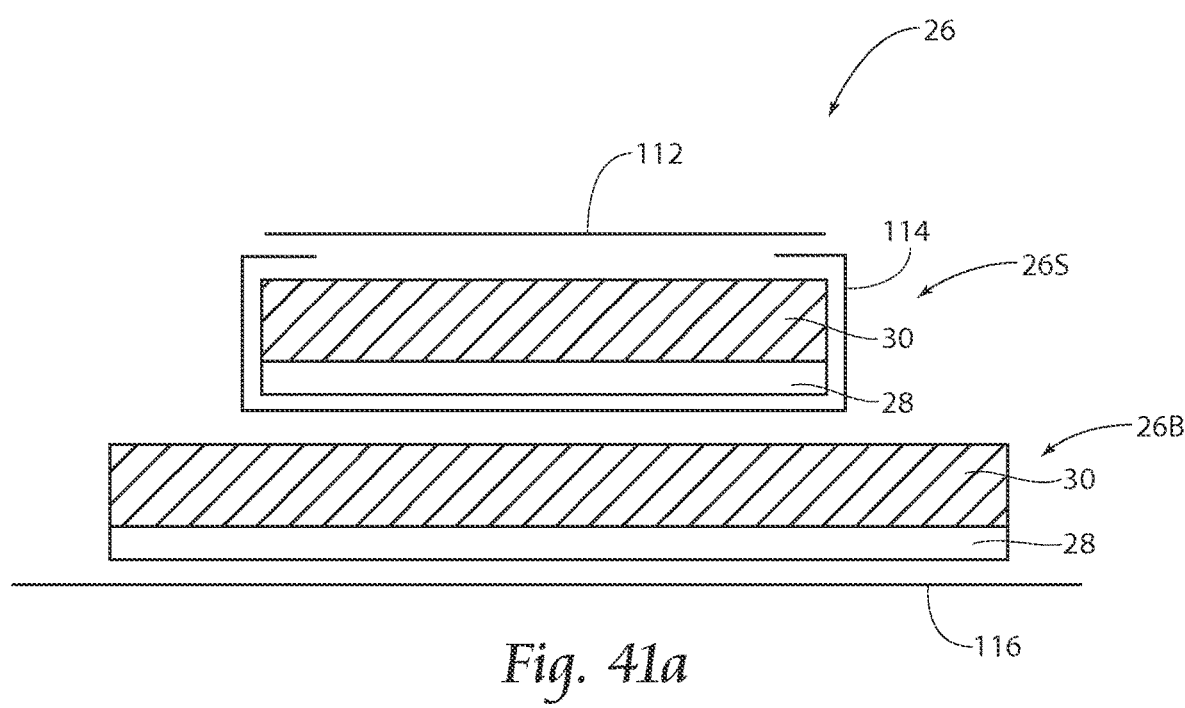
Fig. 41a
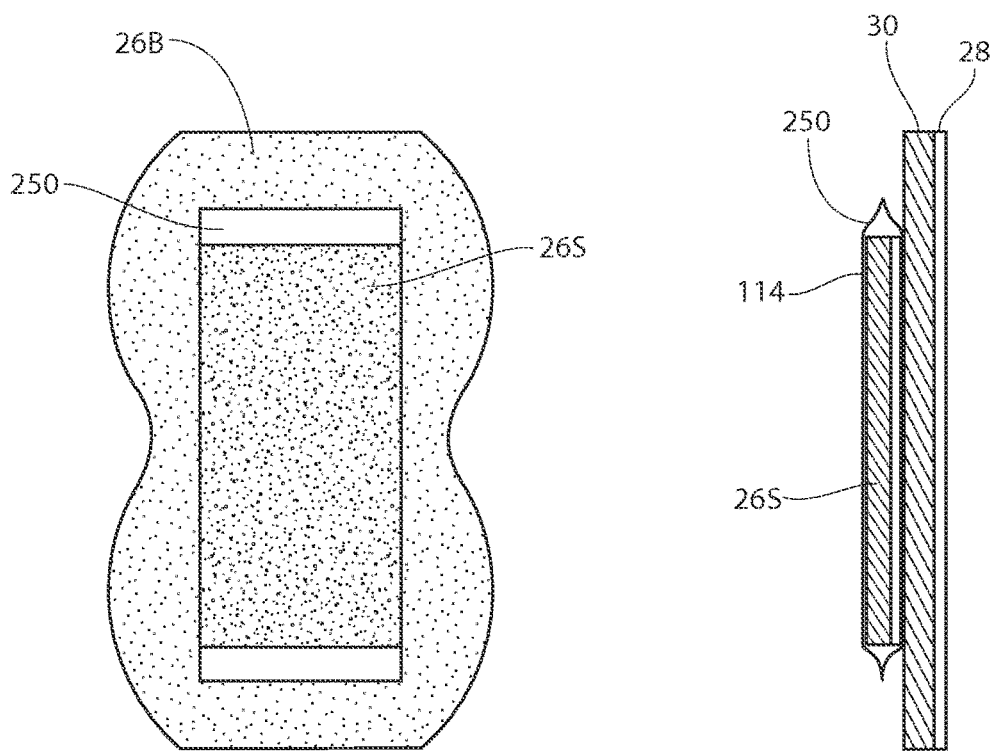
Fig. 41b
Fig. 41c

APPARATUS AND METHOD FOR FORMING ABSORBENT CORES

BACKGROUND OF THE INVENTION

This invention relates to formation of absorbent cores for use in disposable products such as diapers and sanitary napkins.

Sanitary napkins used in feminine hygiene are absorbent items worn by women to recover undesirable bodily discharges. These absorbent articles are typically comprised of an absorbent core sandwiched between layers of woven or non-woven materials.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper (and, oftentimes also in conjunction with feminine hygiene products), multiple roll-fed web processes are typically utilized.

To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calendar unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition web material and a nonwoven web material, both of which are fed from material rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a die roller and a platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slicing is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners.

After the nonwoven web is sliced, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

Generally, disposable undergarments such as pants-type diapers are made up of two nonwoven layers of material with elastic strands of material placed between the two nonwoven layers of material thus creating an elastic web laminate. The layers of material are continuous sheets of material that are eventually cut into individual undergarment lengths. The elastic strands may be arranged and cut so that specific areas of the undergarment are free of elastic tension or forces. An absorbent pad, often contained within an insert or core is then also placed into the pants-type diaper product.

To insure the pants-type diaper retains a proper shape and to hold all of the added layers of the diaper, reinforcing layers and backing materials are normally added to the continuous sheets of material, with the reinforcing layers corresponding to the cut elastic strands of each individual blank. Each of these layers needs to be adhesively joined at some point in the manufacturing process to the elastic web laminate to form the completed undergarment.

Often, void spaces need to be created in the diaper, such as holes cut out of the main web for provided leg holes when the undergarment is ultimately formed. To create the void spaces, the web is ordinarily die cut, with the web severed between a die and an anvil. The portion of the web material that is removed is referred to as a "chip." As the die wears throughout time, the severing of the chip from the web material becomes gradually a duller cut. This complicates the removal of the chip because the severing might not create a continuous cut out chip, with possibly some strands of the web material still coupling the chip with the web. It is desired to lengthen the amount of time and increase the number of chips that a single die can effectively be used for, to reduce the number of die change-outs.

The current practice in applying a stretchable web such as a poly web to a second web involves continuously feeding the poly web into the process which results in poly running full length of product, or alternatively, full length of a constructed insert core which is then placed onto a nonwoven-type chassis. Not all machine configurations can be adapted from a full length poly chassis to a poly insert configuration due to space and/or cost restrictions. It should be understood that application of the poly web along the entire length of the product, rather than only where it is useful, increases the amount of poly material which must be utilized. This is a waste of the material resource and adds additional cost to the product. It is therefore desirable to create a lower cost product by putting stretchable material into the product only where it is useful, instead of the complete product.

This invention relates to the art of vacuum wheels and more particularly to a vacuum wheel vacuum opening configuration that has improved vacuum holding power to hold articles in place.

A vacuum wheel in the form of a rotary member having vacuum holes opening onto a cylindrical outer surface for the support and retention of stretchable film is typically a component of an apparatus that is known for various applications. A common example where an apparatus including a vacuum wheel would be used includes the construction of apparel that is worn on the body such as disposable diapers. In this application, an elastic waistband is stretched before being inserted into the waistband region. An example of such an apparatus is described in U.S. Pat. No. 4,925,520, commonly owned by the assignee hereof and incorporated herein by reference. Absorbent articles including bandages, disposable diapers, and sanitary napkins, generally include an absorbent core that has a multiplicity of components so as to improve the article's absorption and retention characteristics.

Typically, the absorbent fibrous material is composed of cellulose wadding or cellulosic wood pulp material commonly referred to as "fluff", although a mixture of natural and synthetic fibers is within the scope of the invention. An absorbent core composed of wood pulp fluff is typically formed by employing conventional air laying techniques.

These absorbent cores have had their total absorbency improved greatly by the addition of super absorbent material, or super absorbent polymer (SAP) to the commonly used absorbent fibrous materials.

The ability of these absorbent cores to manage the typical surges of liquid flow is heavily dependent on the proper distribution of super absorbent material within the absorbent fluff. When most super absorbent materials absorb aqueous fluids, they swell substantially, often to double their dry dimensions or more at saturation. As these super absorbent materials absorb fluid and swell, they generally become a gelatinous mass.

There has been a trend in reducing the bulk of diapers, in attempts to make them more like underwear and to take up less shelf space in retailer's outlets. Generally, the thinner the diaper, the higher the concentration of super absorbent material required to produce the same level of absorbency. High levels of super absorbent material, however, tend to be more difficult to control and to maintain in position.

In conventional core forming processes, three-dimensional fluff receiving pockets rotate about a vacuum drum. The pockets typically include baffles and screens which permit airflow through the pockets. The fluff is applied to the fluff receiving pockets entrained in air applied to the pockets. The vacuum attracts the fluff to a screen-like mesh that forms the pockets. The fluff is retained by the pockets, and the amount of fluff builds up from the screen forming the pocket. However, some fluff passes through the screen of the pockets and into the vacuum stream that is drawing the fluff into the pocket. Thus, some fluff undesirably becomes entrained in the vacuum stream.

In the core forming process, it is required to balance the amount of air urging the fluff towards the core forming pocket and the amount of vacuum used to retain the fluff within the pocket. Machine processes have become more complex as speeds of machines have increased, so air handling systems used in this process have greater demands placed on them. For instance, if the machine is running faster, pulp is required to be delivered to the core forming pocket quicker, necessitating a greater air flow to the pocket. To deliver more pulp to the pocket, more vacuum is required to retain the pulp within the pocket. One complication is in achieving optimum balance between air in to the pocket and vacuum applied to the back side of the pocket.

Imbalance between the amount of air supplying pulp to the core forming pocket and vacuum applied to the back of the pocket, holding the fluff in, causes puffs of fluff to escape forming chamber. Conventional core forming technology allows for limited adjustability to try and achieve the optimum balance between air in and vacuum. The largest air delivery is from fiberizing mill which supplies fluff and blows the fluff into the core forming chamber.

Another source of air into forming process is from the dust collection equipment, which returns collected fluff from the vacuum stream to the core forming drum. Beginning with fluff that passes through the core forming pocket, the vacuum stream leads the fluff within the vacuum stream to the dust collection unit. A filter within the dust collection unit captures this fluff, this fluff is removed from the filter, and recirculated into the core forming process. Typically, this vacuum stream is fed into a drum filter housing, such as described in U.S. Pat. No. 5,679,136, commercial embodiments of which are available from the Osprey Corporation, and which is incorporated herein by reference.

The process of removing dust off of the filter uses a high volume of air. It must collect all of the dust, and return the fluff dust to core forming ducting. When the diaper making machine is stopped, it is undesirable to return fluff to the core forming process, because the core forming process is on hold until regular operation resumes. Ordinarily, in a shut down situation, the vacuum off of the filter in the dust collection unit is still operating, and collected fluff or dust gets diverted to a main drum filter. This process forms a closed loop recirculation while machine is idle. However, components of the system, such as a nozzle fan, end up beating the recirculated pulp into a fine powder, and this is undesirable because the powdered fluff lacks fluid retaining characteristics.

Other sources of air delivery to the forming chamber include the SAP delivery system, and air-bleed openings in the forming chamber itself.

It is desired to reduce air flow from the dust return system in order to achieve greater adjustability to try and achieve the optimum balance between air in and vacuum. It is also desired to reduce the destruction of recirculated pulp to obtain better fluid retaining characteristics.

SUMMARY OF THE INVENTION

In general terms, the invention comprises several variations of core formation techniques, including a large and small discrete core, formed on a screen and combined; a large and small continuous core, formed on a web; and a single two or three-dimensional core formed on a screen or formed on a web. Additionally, and pre-made air-laid web on or in or between or under several core variations are disclosed. Of course, various combinations of the above methods and apparatus can be combined to form additional variations.

This invention relates to a method and apparatus for forming an absorbent core or cores. More particularly, the present invention relates to a method and apparatus for withdrawing fibrous material from a core forming drum, separating the fibrous material from an air stream, and forming the core from fibrous material and super absorbent polymers into different configurations. Cores can be paired together to form a core of different profile, and cores can be wrapped individually and placed and combined.

A method of forming an absorbent core comprising forming a first core having a first fluff layer and a second super absorbent polymer and fluff mixture layer at a first speed, forming a second core having a first fluff layer and a second super absorbent polymer and fluff mixture layer at a second speed, debulking and scarfing said first and second cores, accelerating the second, smaller core from the second speed to substantially match the first speed, and combining the first and second cores is disclosed.

Said first core can have a contoured figure such as a peanut shaped figure (FIG. 15), and said second core can a substantially rectangular figure, and said second core can be smaller than said first core.

The combined first and second cores are deposited onto a top side of a carrier layer traveling at substantially said first speed.

The fluff layers and fluff/SAP layers can be alternated, and either can be placed face down onto said carrier layer.

One or both of said first or said second cores can be wrapped with a material layer prior to deposition on said carrier layer.

Either the first or the second core can be placed directly onto the carrier layer. Either of the fluff layers and fluff/SAP layers of the first or second cores can be placed directly onto the carrier layer. In one embodiment, the first core is made by a first forming drum and said second core is made by a second forming drum. Alternatively, the second core and is made by a first forming drum and the first core is made by a second forming drum. Still alternatively, at least one of said first core and said second core are formed from a pre-made, air-laid material.

The cores can either be of similar size, or a bigger/smaller arrangement, and can be similar or different shapes.

Cores can either be formed on a pocket type core forming drum, or a single circumferential pocket on a core forming drum can be used, and then discrete core pieces from a continuous strip of core material can be severed by a core knife.

Three dimensional cores are also disclosed, in which the core has a width, a length, and at least two different heights.

To summarize the core element variables, the core element variables can include two dimensional cores (uniform thickness or height), or three dimensional cores (variable thickness or height).

Core layering can be achieved by a full fluff/SAP blend, providing a first dusting or fluff layer under or over the fluff/SAP blend, providing a first and second dusting or fluff layers under and over the fluff/SAP blend, and providing a core formed of just fluff.

Next, the cores can be formed on a screen or on a web.

Next, the cores can be discrete and unwrapped, discrete and wrapped, discrete and wrapped with the wrap longer than the core and glued to form a teabag type structure (in this embodiment the wrap is cut). The cores can also be continuous and unwrapped and cut, continuous and wrapped and cut, or the cores can be continuous and continuously wrapped, and both the core and the wrap are cut.

BRIEF DESCRIPTION OF THE DRAWINGS

FIGS. 39-41 describe formation of a dual core, with a larger, non-wrapped core structure laid upon a poly layer, topped by a tissue-wrapped small core structure;

FIG. 39 is a schematic of an alternate embodiment of the present invention, with a larger, non-wrapped core structure laid upon a poly layer, topped by a tissue-wrapped small core structure, and then passed downstream for further processing;

FIG. 40 is a side view of a large and small discrete core forming unit, with a larger, non-wrapped core structure laid upon a poly layer, topped by a tissue-wrapped small core structure, and then passed downstream for further processing;

FIG. 41a is a cross sectional view of a larger, non-wrapped core structure laid upon a poly layer, topped by a tissue-wrapped small core structure;

FIGS. 41b and 41c are plan and cross sectional views of an alternative embodiment of the product shown in FIG. 41a, respectively;

FIG. 42 is a schematic of an alternate embodiment of the present invention, with a small, tissue-wrapped core structure laid upon a poly layer, topped by a non-wrapped larger core structure, and then passed downstream for further processing;

FIG. 43 is a side view of a large and small discrete core forming unit, with a small, tissue-wrapped core structure laid upon a poly layer, topped by a non-wrapped larger core structure, and then passed downstream for further processing;

FIG. 44 is a cross sectional view of a with a small, tissue-wrapped core structure laid upon a poly layer, topped by a non-wrapped larger core structure;

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
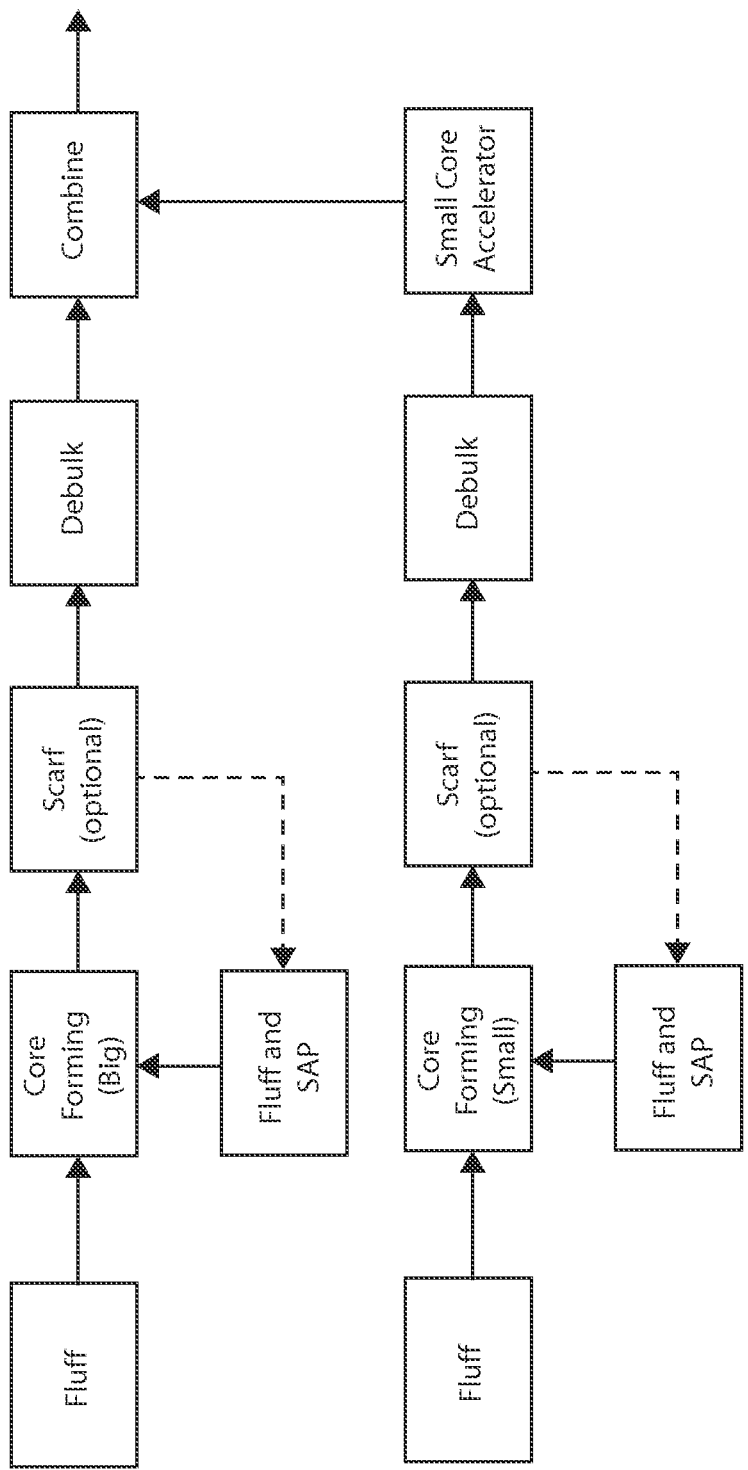
FIG. 1 is a schematic of one embodiment of the present invention, a large and small discrete core, formed on a screen and combined, and then passed downstream for further processing.

Referring now to FIG. 1, a schematic of one embodiment of the present invention, a large and small discrete core, formed on a screen and combined, and then passed downstream for further processing is shown. As can be seen, two simultaneously operating core forming units, one big and one small, are used to form a big core and a small core, both preferably comprised of fluff and SAP. The small core is accelerated to match the speed of the large core prior to downstream processing.

Figure 2:
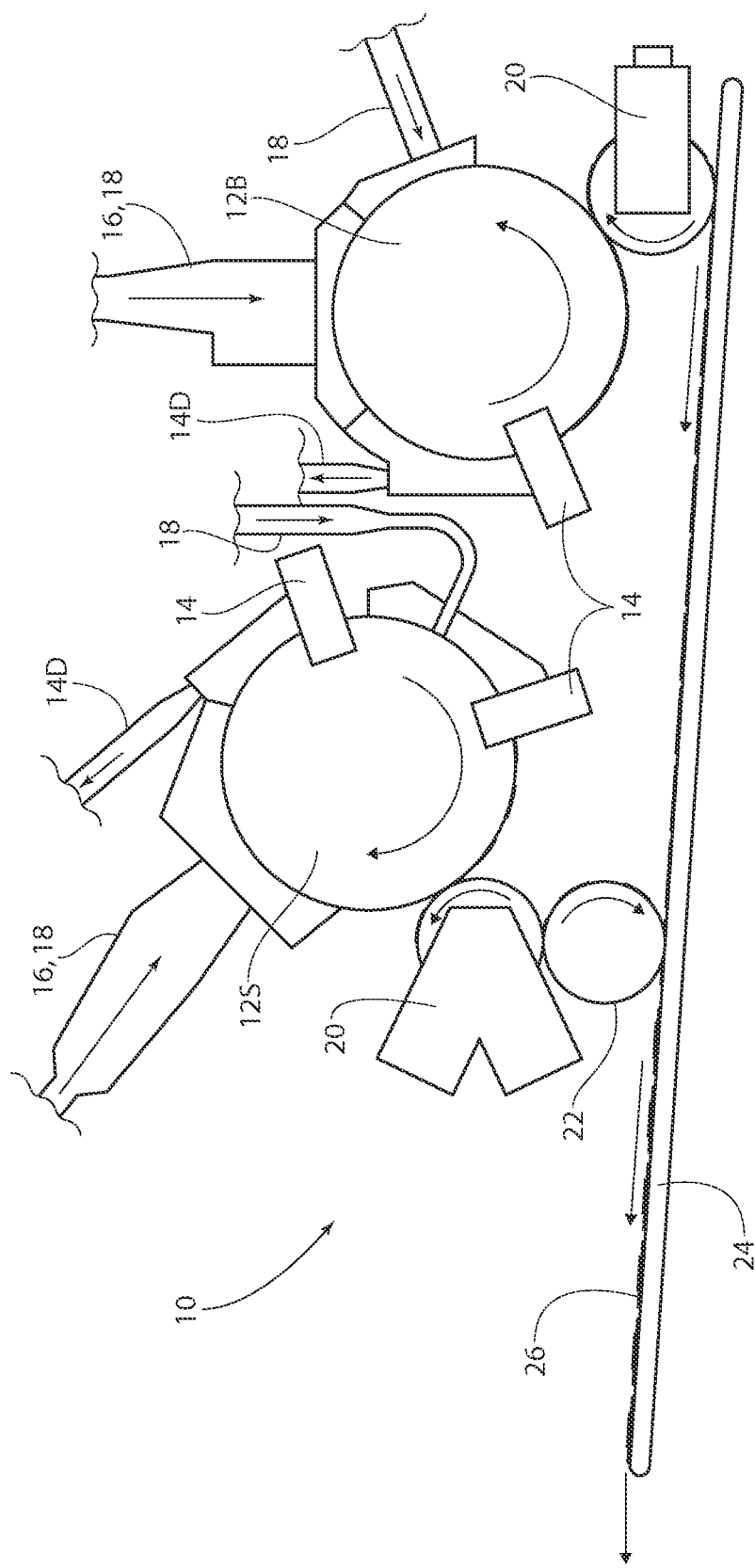
FIG. 2 is a front view of a large and small discrete core forming unit, formed on a screen and combined, and then passed downstream for further processing.

Referring now to FIG. 2, a side view of a large and small discrete core forming 10 units is shown.

Figure 3:
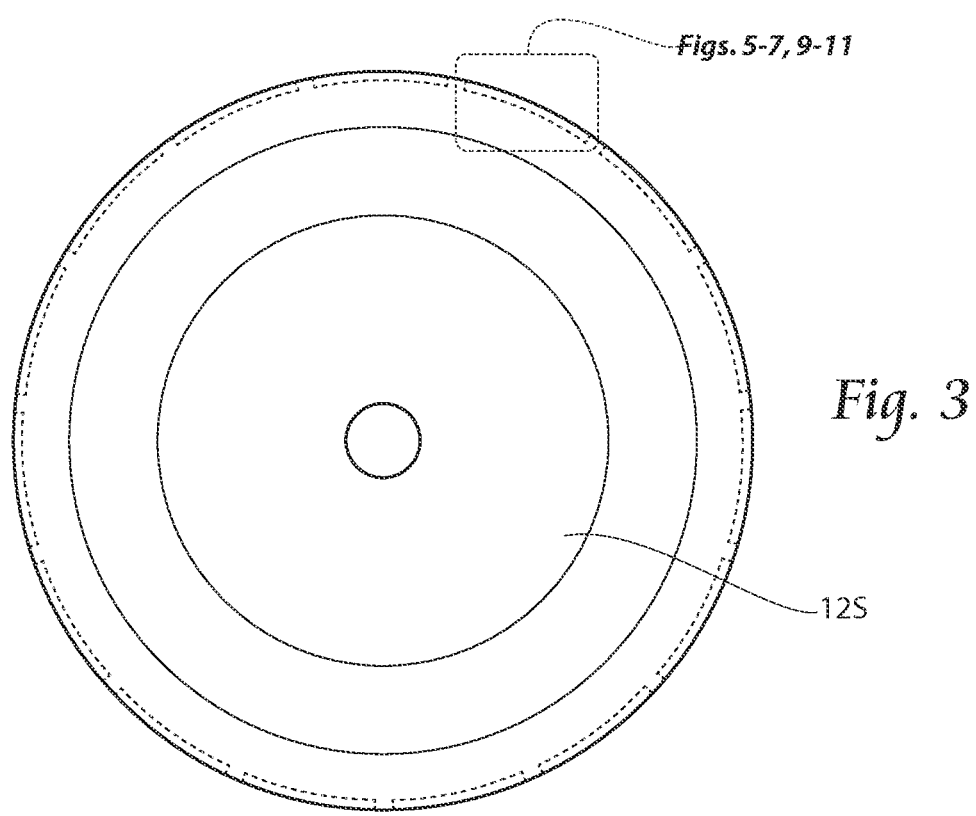
FIG. 3 is a side view of a drum for forming a large and small discrete core, formed on a screen and combined, and then passed downstream for further processing.
Figure 8:
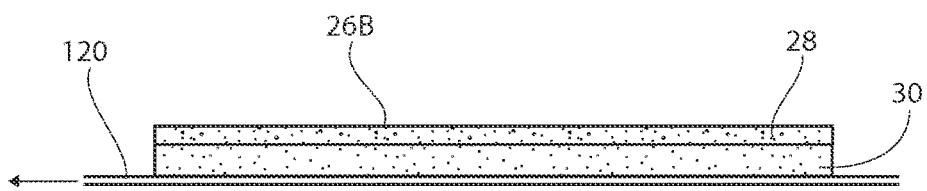
Figure 9:
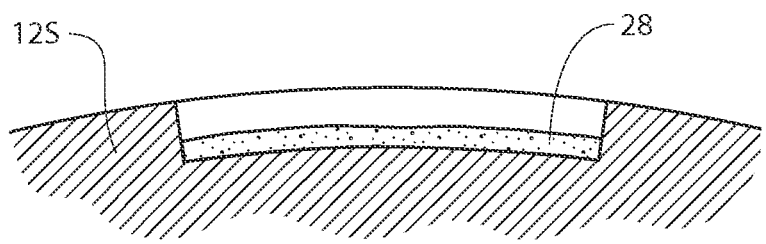
Figure 10:
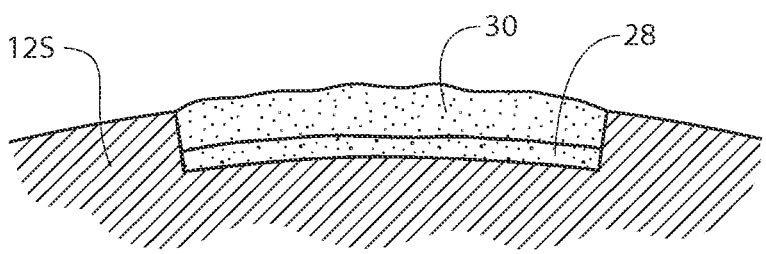
Figure 11:
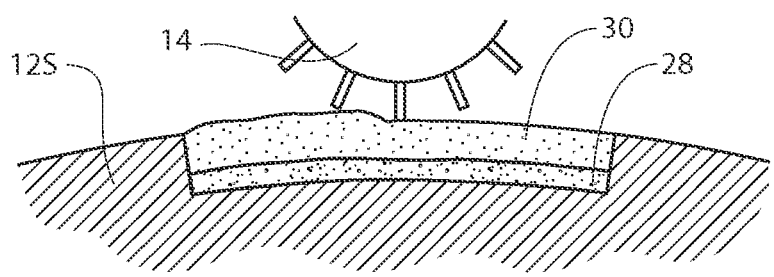
Figure 12:
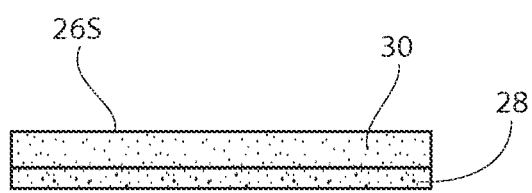

A small core forming drum 12S (to form small cores) is first, followed by a big core forming drum 12B (to form big cores). Both of these drums 12S and 12B receive a first layer of dust or fluff/SAP mixture 30 from Fluff/SAP introduction unit 16, onto a pocketed drum 12S or 12B, shown in side view in FIG. 3. Processes on the drums can include fluff and sap deposition, scarfing, fluff deposition, and another scarfing operation. The core can be scarfed by scarfing unit 14, which discharges and recycles the scarfed material back into the system through discharge 14D. Next, an additional layer of fluff 28 from fluff introduction unit 18 is applied atop the SAP/Fluff mixture. One purpose of the addition of an independent fluff layer 28 is to isolate SAP from contacting unintended surfaces, because the SAP can have a tendency to be abrasive and migrate. This sequence is depicted in FIGS. 5-8 for formation of the big core 26B, and FIGS. 9-12 for formation of the small core 26S. In FIGS. 5-8, a SAP/Fluff mixture 30 is first deposited (FIG. 5), and scarfed by scarfing unit (FIG. 6), next a fluff layer 28 is deposited and scarfed (FIGS. 7a and 7b) and then deposited onto running web 120 (FIG. 8).

Figure 4A:
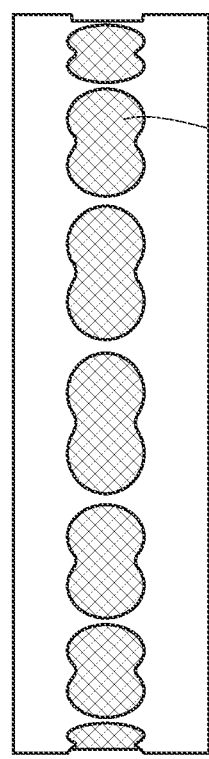
FIGS. 4A and 4B are plan views of cores formed according to the present invention.
Figure 4B:
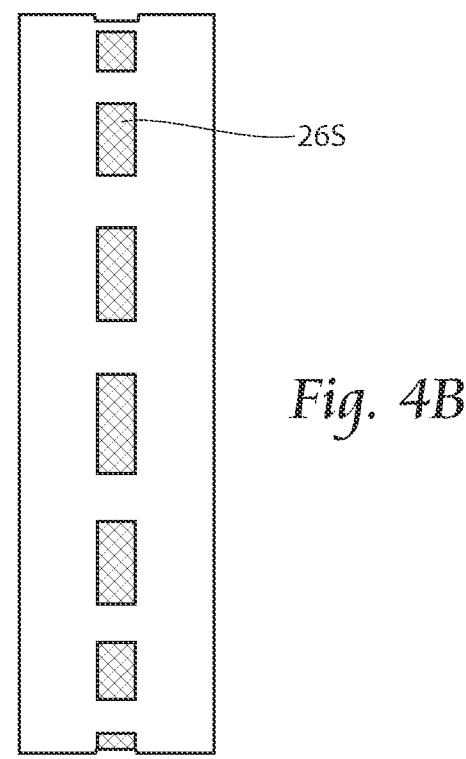
Figure 5:
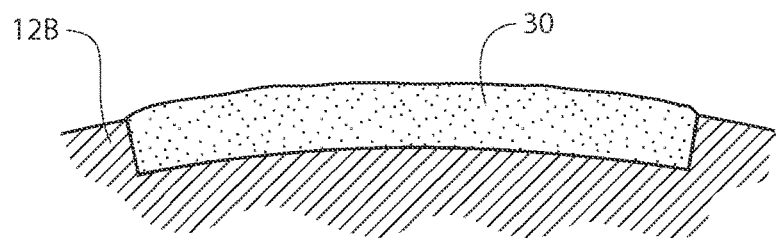
FIGS. 5-12 are side views of a core structure deposition and scarfing operation.
Figure 6:
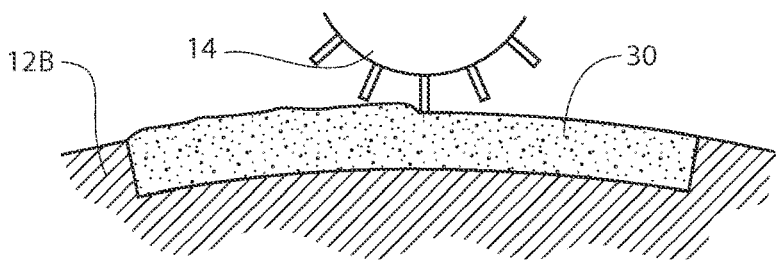
Figure 7A:
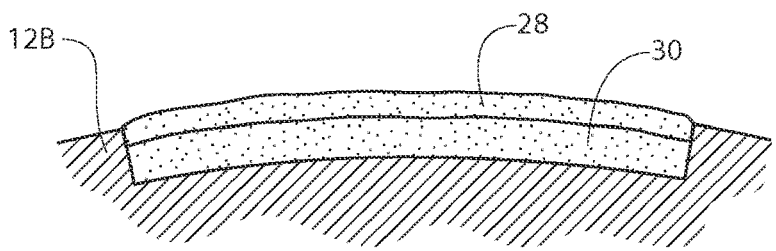
Figure 7B:
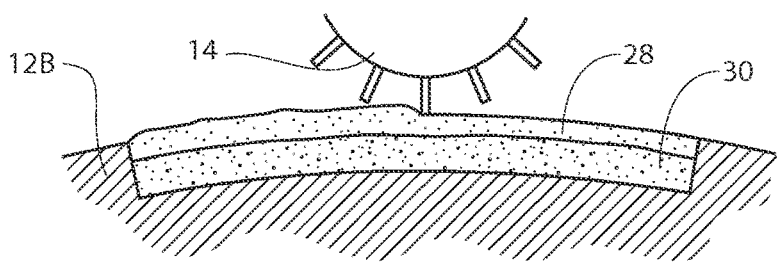

The big core forming drum 12B deposits a big core 26B onto a conveyor 24 following debulking unit 20 (FIG. 4a), and after being carried downstream, it receives, after an optional scarfing unit 14, the small core 26S which can be passed through debulking unit 20 and then to a core acceleration unit 22 to match speeds with the big core 26B (FIG. 4B).

Figure 13:
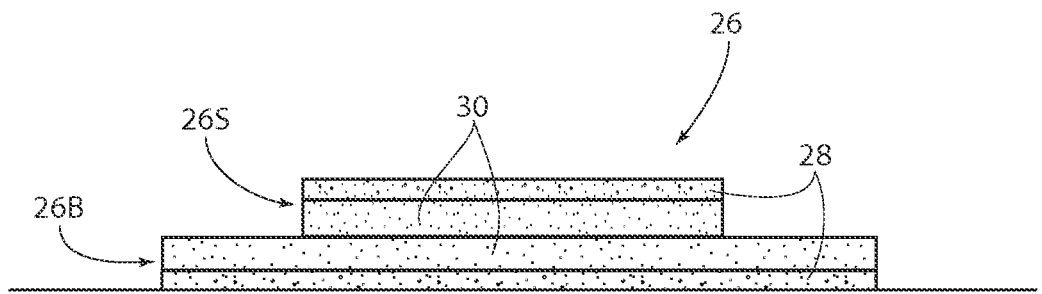
FIG. 13 is a side view of an assembled core.
Figure 14:
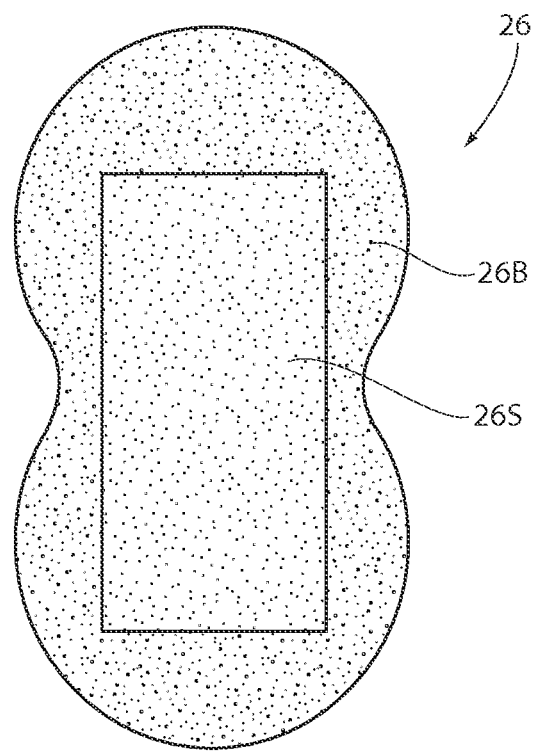
FIG. 14 is a plan view of an assembled core.

Referring to FIGS. 13 and 14, a side and top view of an assembled core 26 is shown. As can be seen, the core comprises essentially four layers: the small core 26s having a SAP/Fluff mixture 30 on top, and a fluff layer 28, the large core 26B likewise having a SAP/Fluff mixture 30 on top, and a fluff layer 28. This assembled core is then passed downstream for further processing as desired. As can be seen in FIG. 14, in one embodiment the core 26B is contoured in a peanut-shaped configuration.

Figure 15:
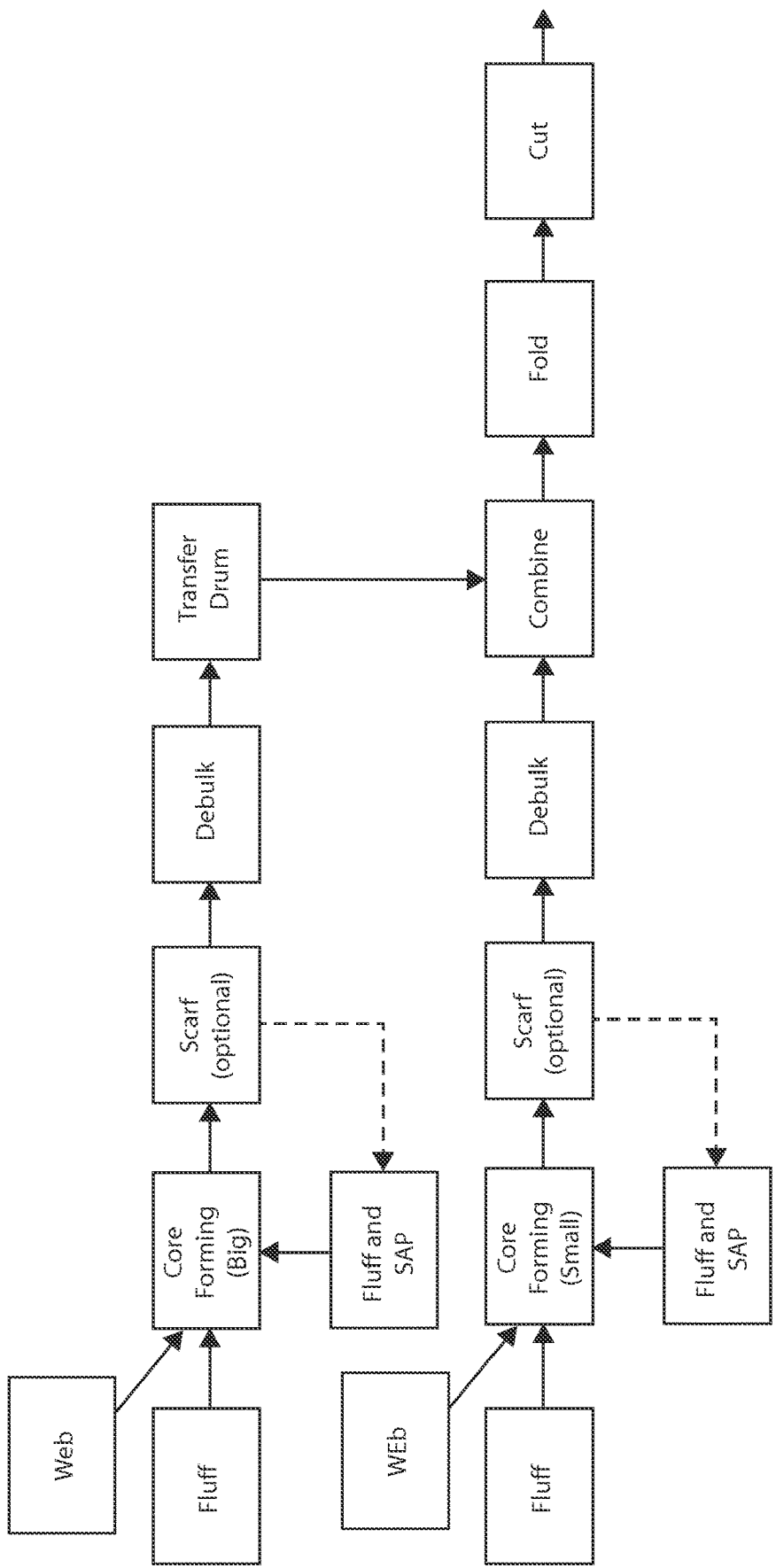
FIG. 15 is a schematic of a second embodiment of the present invention, a large and small continuous core, formed on a web.

Referring now to FIG. 15, a schematic of a second embodiment of the present invention is shown, a large and small continuous core, both formed on a web.

Figure 16:
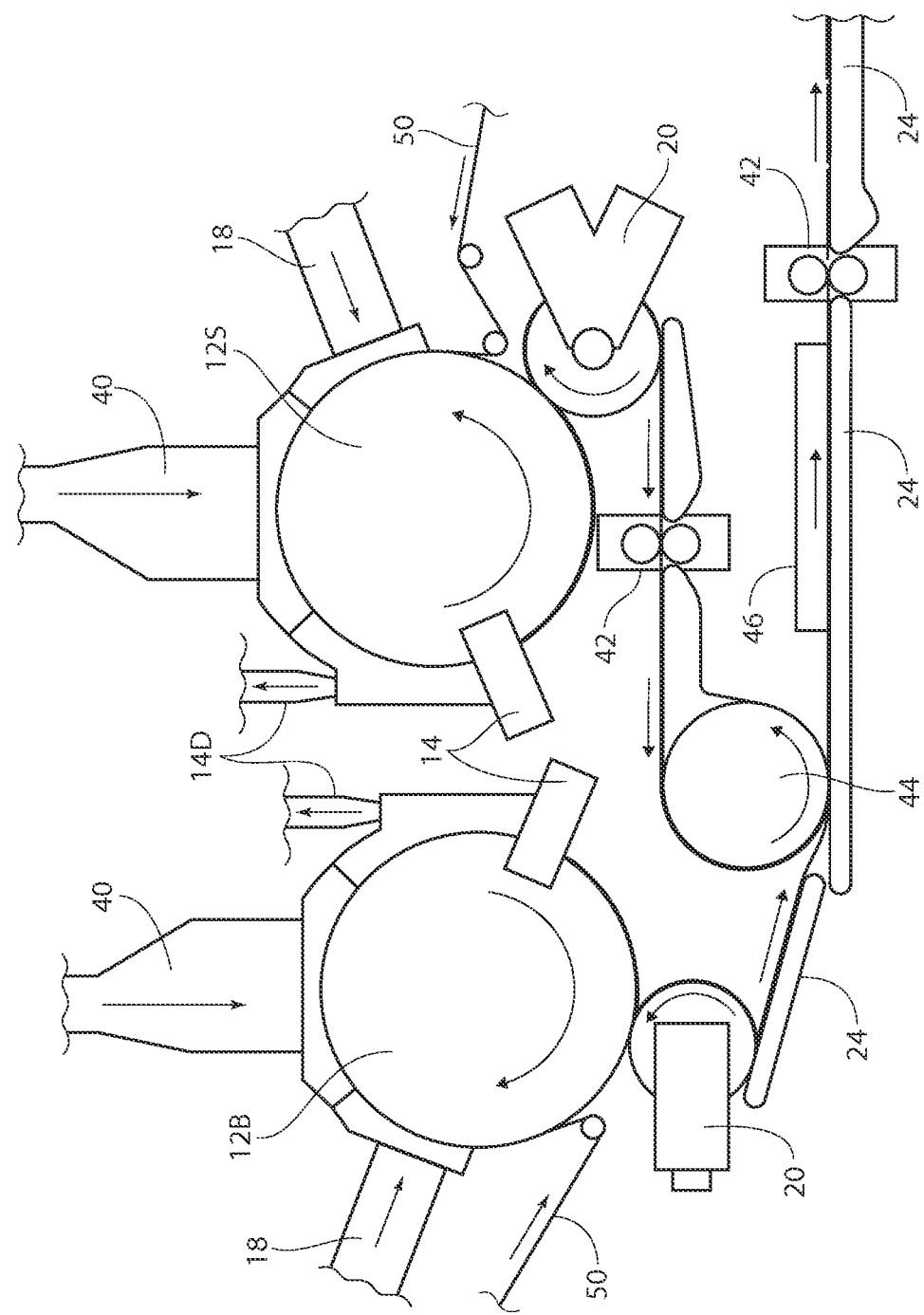
FIG. 16 is a side view of a large and small discrete core forming unit, a large and small continuous core, formed on a web.
Figure 17:
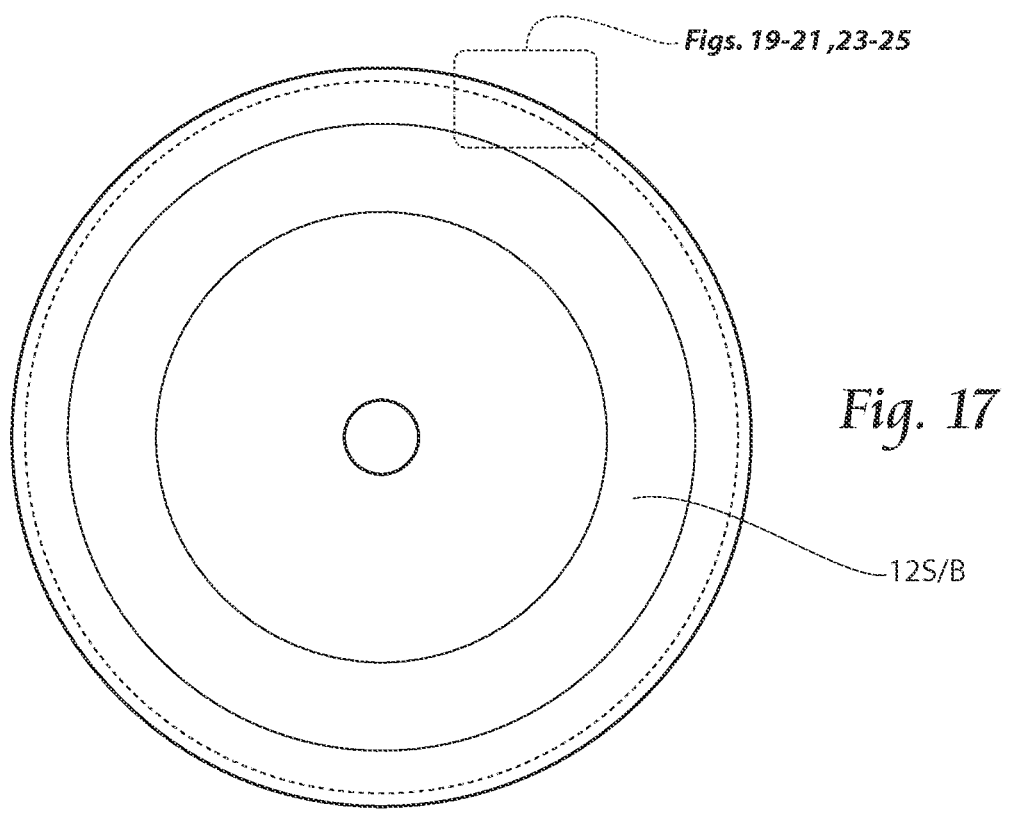
FIG. 17 is a side view of a drum for forming a large and small continuous core, formed on a web.
Figure 18A:
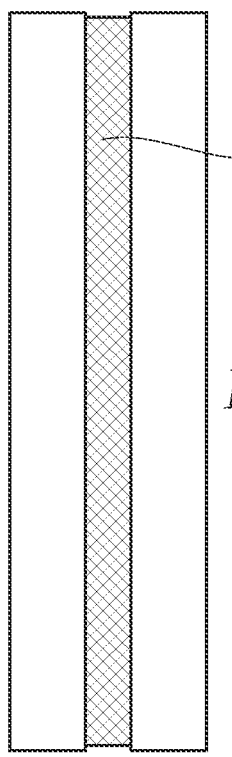
FIGS. 18A and 18B are plan views of a large and small continuous core, formed on a web formed according to the present invention.
Figure 18B:
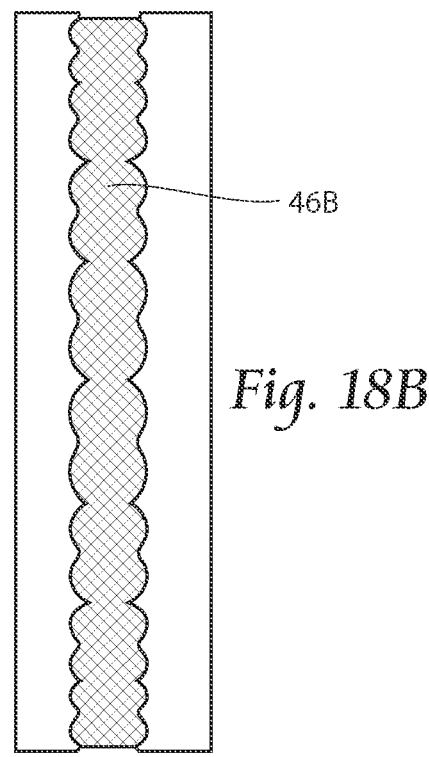
Figure 19:
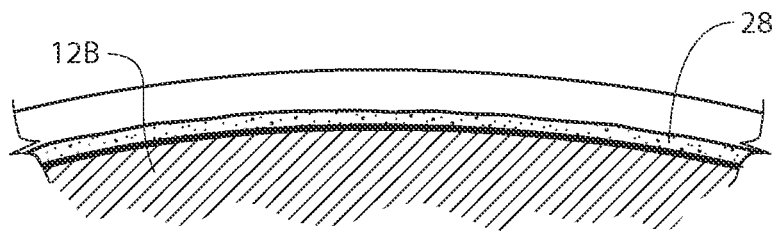
FIGS. 19-26 are side views of a scarfing operation.
Figure 20:
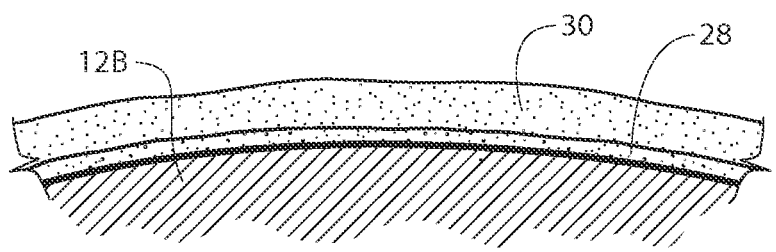
Figure 21:
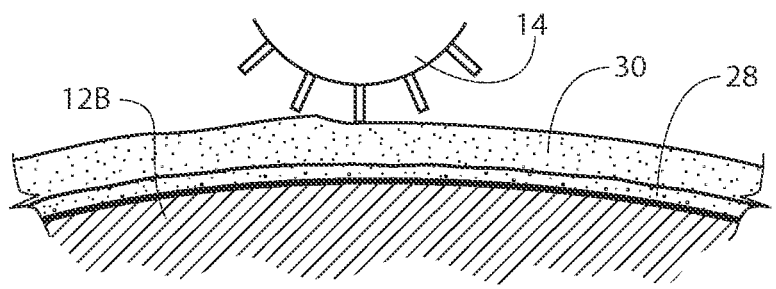
Figure 22:
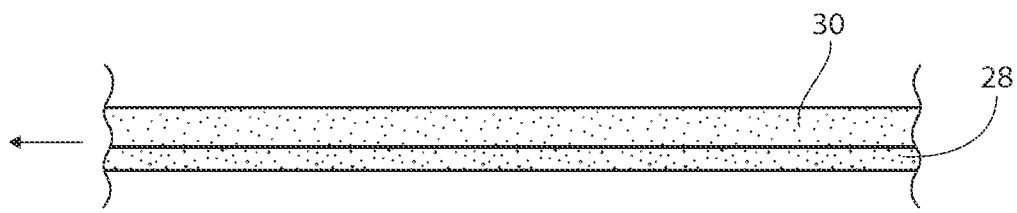
Figure 23:
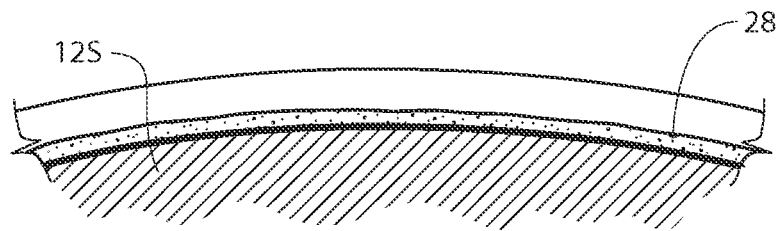
Figure 24:
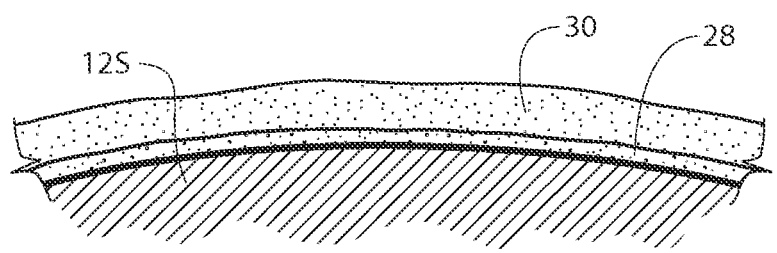
Figure 25:
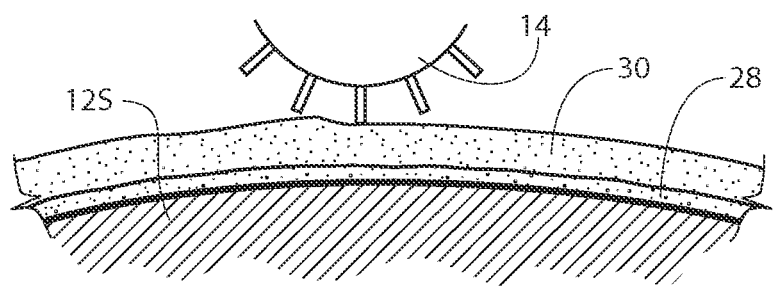
Figure 26:
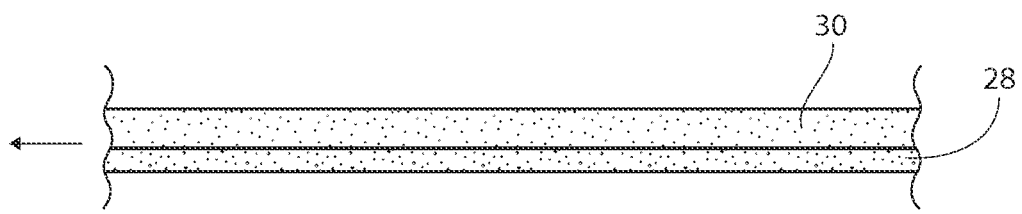
Figure 27:
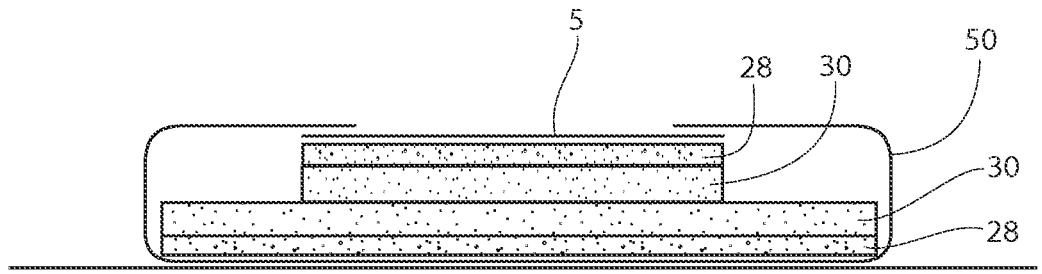
FIG. 27 is a side view of an assembled large and small continuous core.
Figure 28:
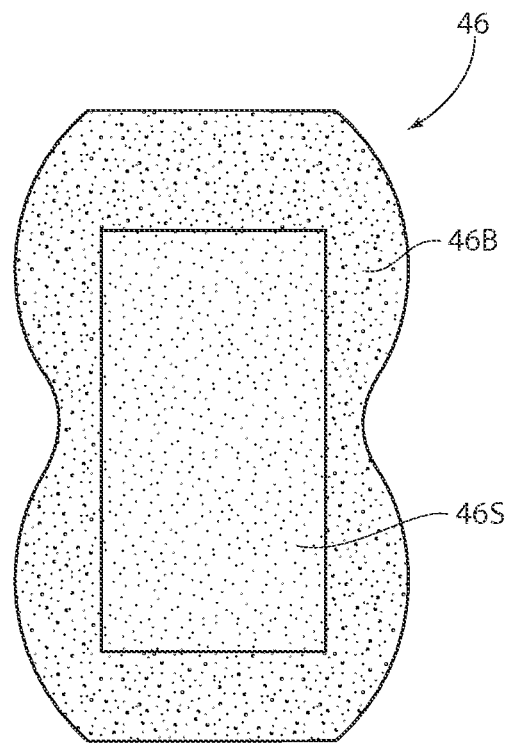
FIG. 28 is a plan view of an assembled large and small continuous core.

Referring now to FIG. 16, a side view of a large and small discrete core forming unit, a large and small continuous core, formed on a web is shown. The first step in the sequence of formation of both the big and small cores is introduction of a non-woven web 50. Atop this layer is applied fluff 28 by fluff introduction unit 18. Next, SAP/fluff mix 30 is applied through the SAP/Fluff introduction system 40. An optional scarfing unit 14 can be used (recycled scarf material recycled through scarf recycling pathway 14D), followed by a debulking unit 20. As can be seen in FIG. 17, the drums 12B and 12S of this system can have a continuous pocket for forming a running web of continuous core material (cut to discrete core pieces by a core knife, described later). As shown in FIGS. 18A and 18B, plan views of a big and small continuous core 46B and 46S respectively are so formed. The scarfing operations of FIGS. 19-26 are side views of a scarfing operation which are optionally used on the uncovered sides of the cores 46B and 46S. A core is formed as shown in FIGS. 27 and 28, essentially to individually wrapped cores 46B and 46S.

During formation of the small core 46S, the continuous core is cut after formation using anvil/knife unit 46, and speed matched by rotating drum 44 and applied atop continuous web 46B. The continuous web 46B (now carrying severed small cores 46S) is then cut with knife 42, completing formation of the discrete cores 46 for further downstream processing.

Figure 29:
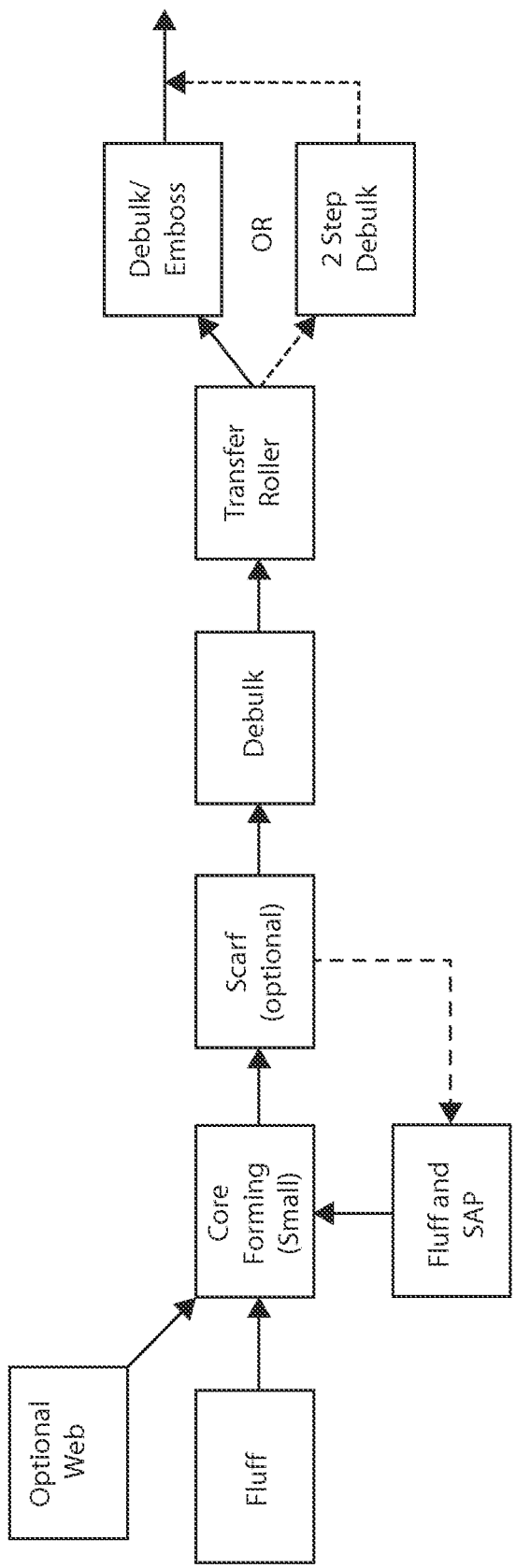
FIG. 29 is a schematic of a third embodiment of the present invention, a single three-dimensional core formed on a screen, and then passed downstream for further processing.

Referring now to FIG. 29, a schematic of a third embodiment of the present invention, a single two or three-dimensional core formed on a screen (and/or formed on web), and then passed downstream for further processing is shown.

Figure 30:
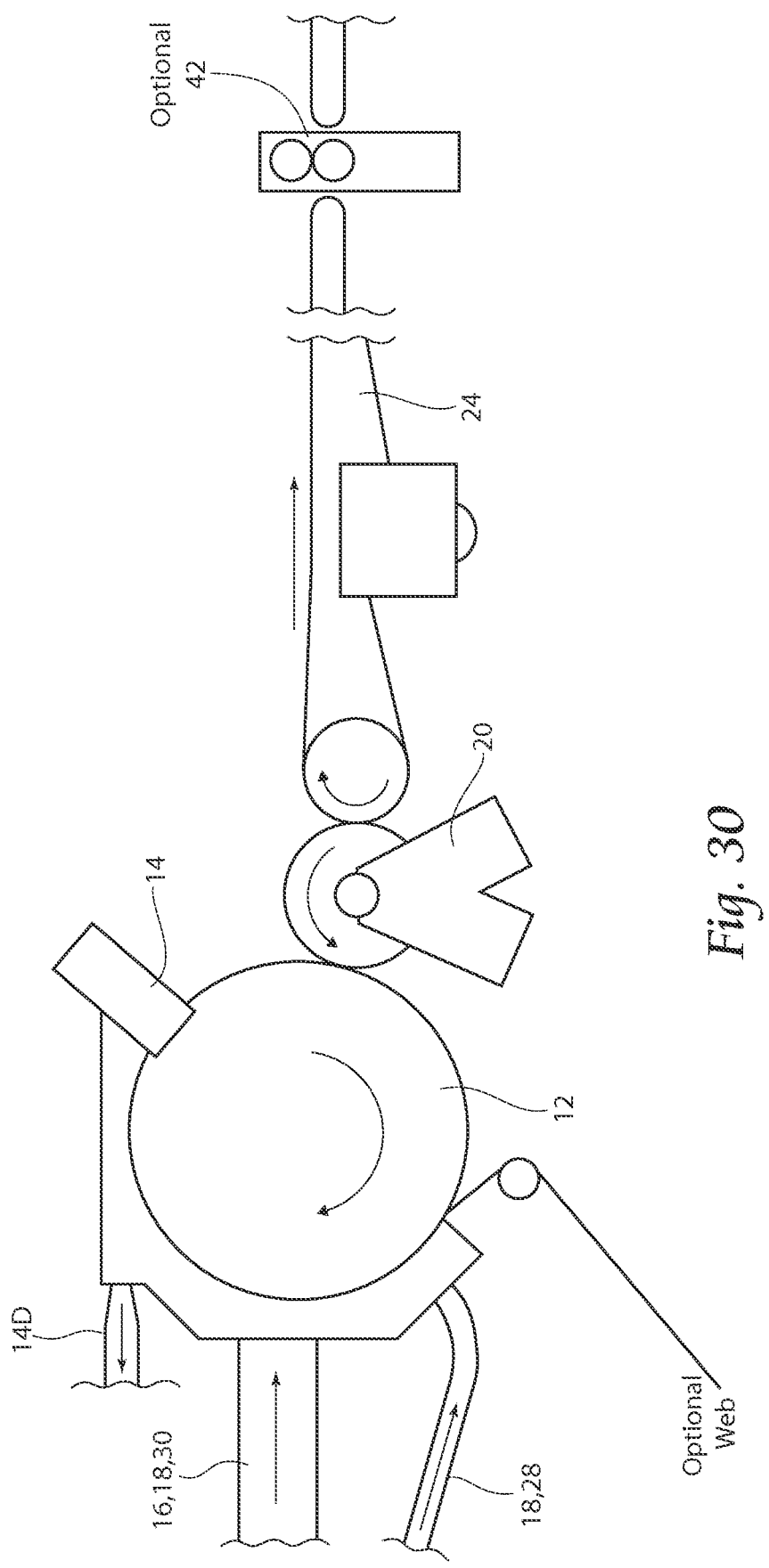
FIG. 30 is a side view of a single three-dimensional core formed on a screen core forming unit.
Figure 31:
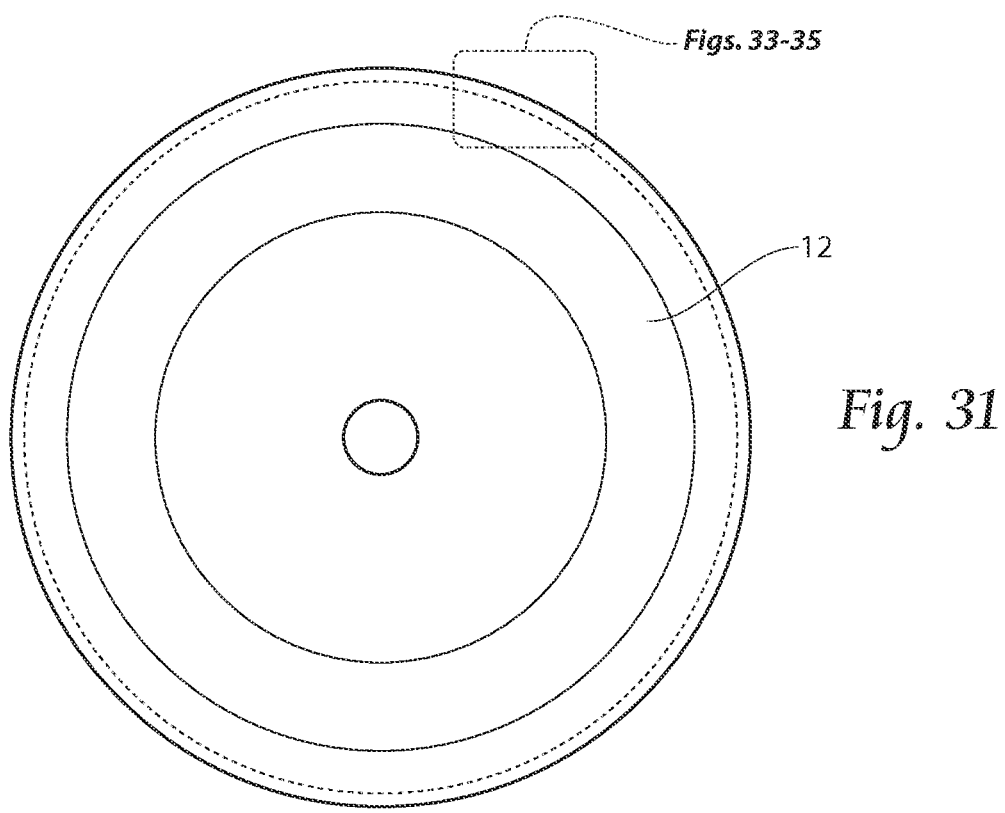
FIG. 31 is a side view of a drum for forming a a single three-dimensional core formed on a screen.
Figure 32:
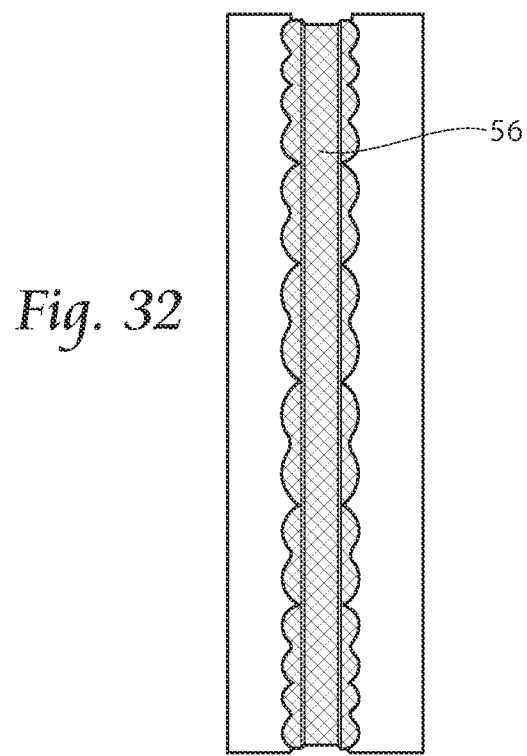
FIG. 32 is a plan view of a large and small continuous core, formed on a web formed according to the present invention.
Figure 33:
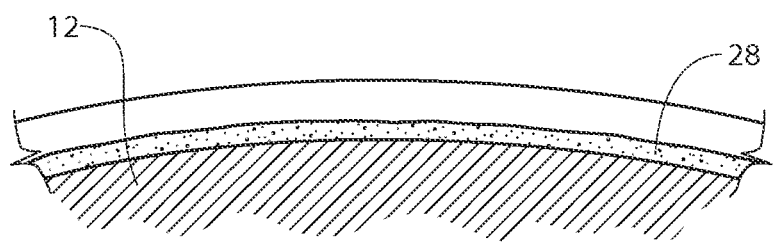
FIGS. 33-36 are side views of a scarfing operation.
Figure 34:
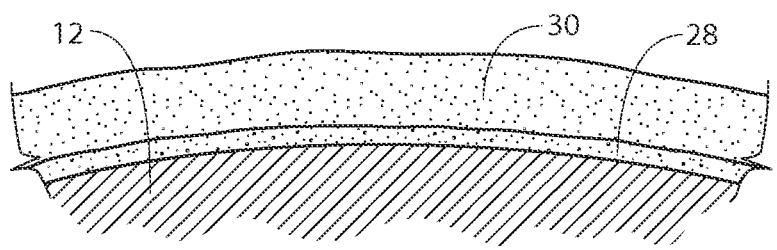
Figure 35:
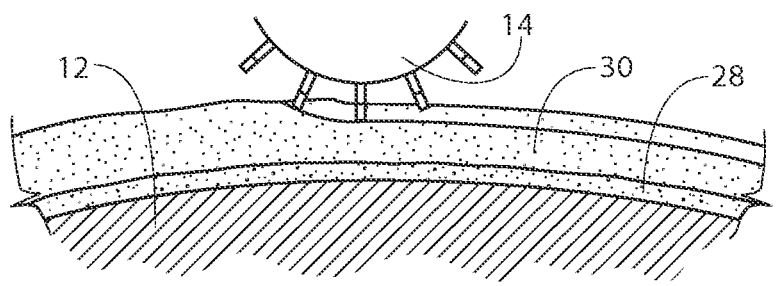
Figure 36:
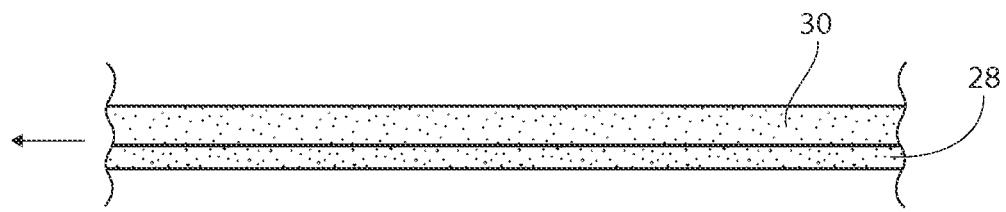
Figure 37:
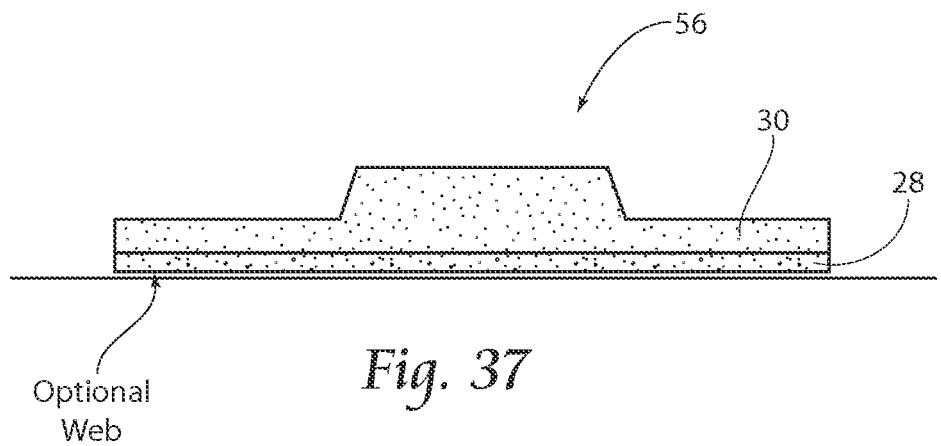
FIG. 37 is a side view of an assembled single three-dimensional core formed on a screen.
Figure 38:
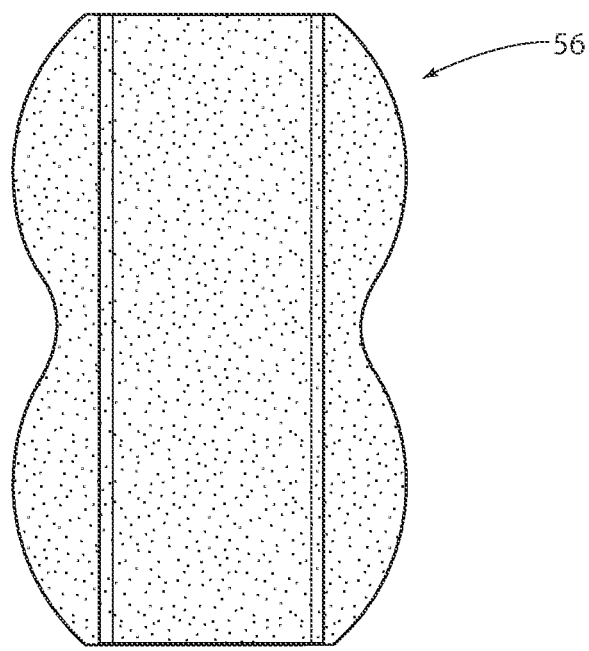
FIG. 38 is a plan view of an assembled single three-dimensional core formed on a screen.

In this embodiment, as shown in FIG. 30, a side view of a single three-dimensional core formed on a screen core forming unit, a first fluff layer 28 from the fluff introduction unit 18 is deposited onto the drum 12 (with a three dimensional pocket, FIG. 31), followed by SAP/Fluff mixture 30 through introduction unit 16/18. Scarfing unit 14 is employed followed by a transfer roll 20, (debulking/embossing, or two debulking units, and an optional knife 42). The scarfing unit 14 of this embodiment could scarf outer boundaries of the composite core 56 (FIG. 32), or a debulker could compress the shape by a pocket component to result in the three-dimensional, two layer profile shown in FIG. 37 (shown in plan on FIG. 38). In the embodiment of FIGS. 37 ad 38, the cores have identical lengths (from top to bottom). The bottom core has a larger width (side to side), but the top core can have at least two different heights (seen in FIG. 37) to form a three dimensional core.

In summary, either a one drum or a two drum unit can be employed to form cores of the present invention. The drums can be either shaped, homogenous, and a dust layer can be employed where desired. A form-on tissue method can be employed for either the small core, the large core, a single wrap or both. Debulking and placing can also be combined as desired to form a desired core.

Referring now to FIGS. 39-41a, formation of a dual core, with a larger, non-wrapped core structure laid upon a poly layer, topped by a tissue-wrapped small core structure is described.

Figure 39:
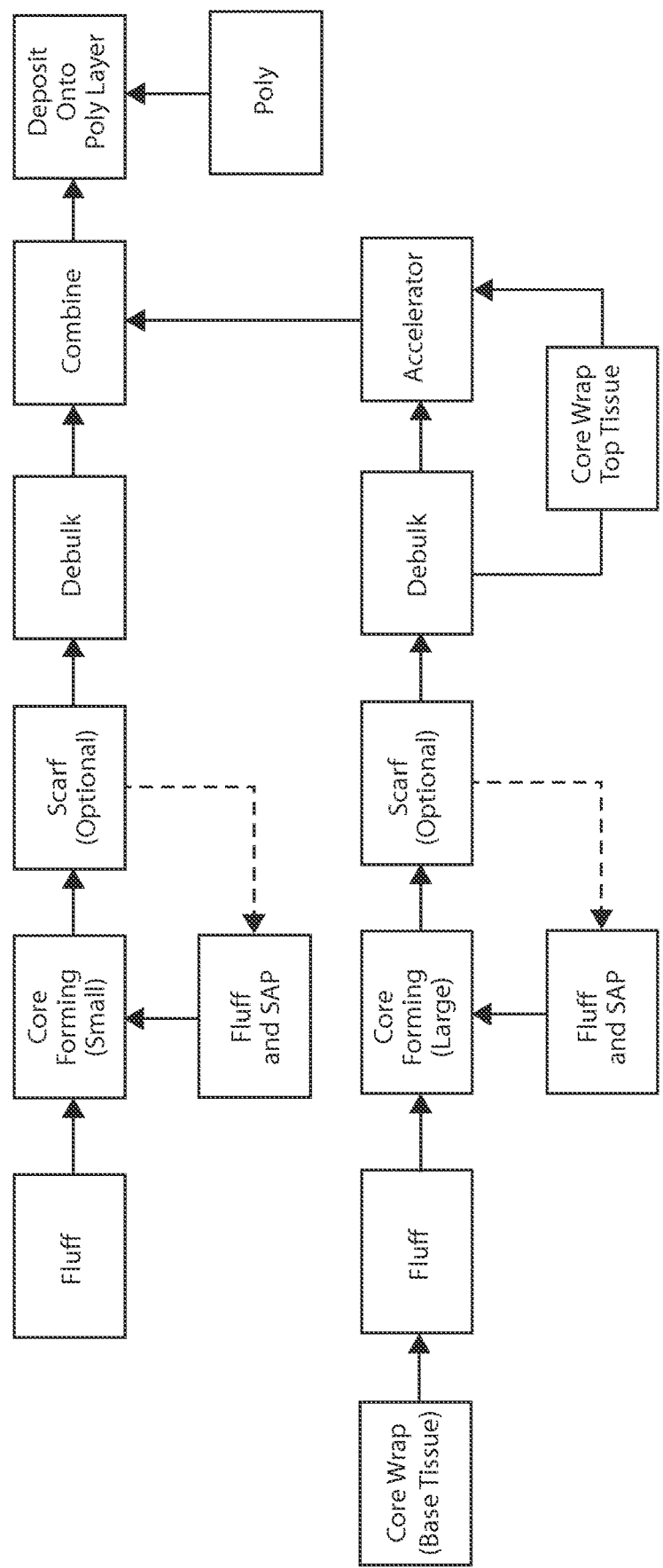

Referring specifically to FIG. 39, a schematic of an alternate embodiment of the present invention is shown, with a larger, non-wrapped core structure laid upon a poly layer, topped by a tissue-wrapped small core structure, and then passed downstream for further processing.

Figure 40:
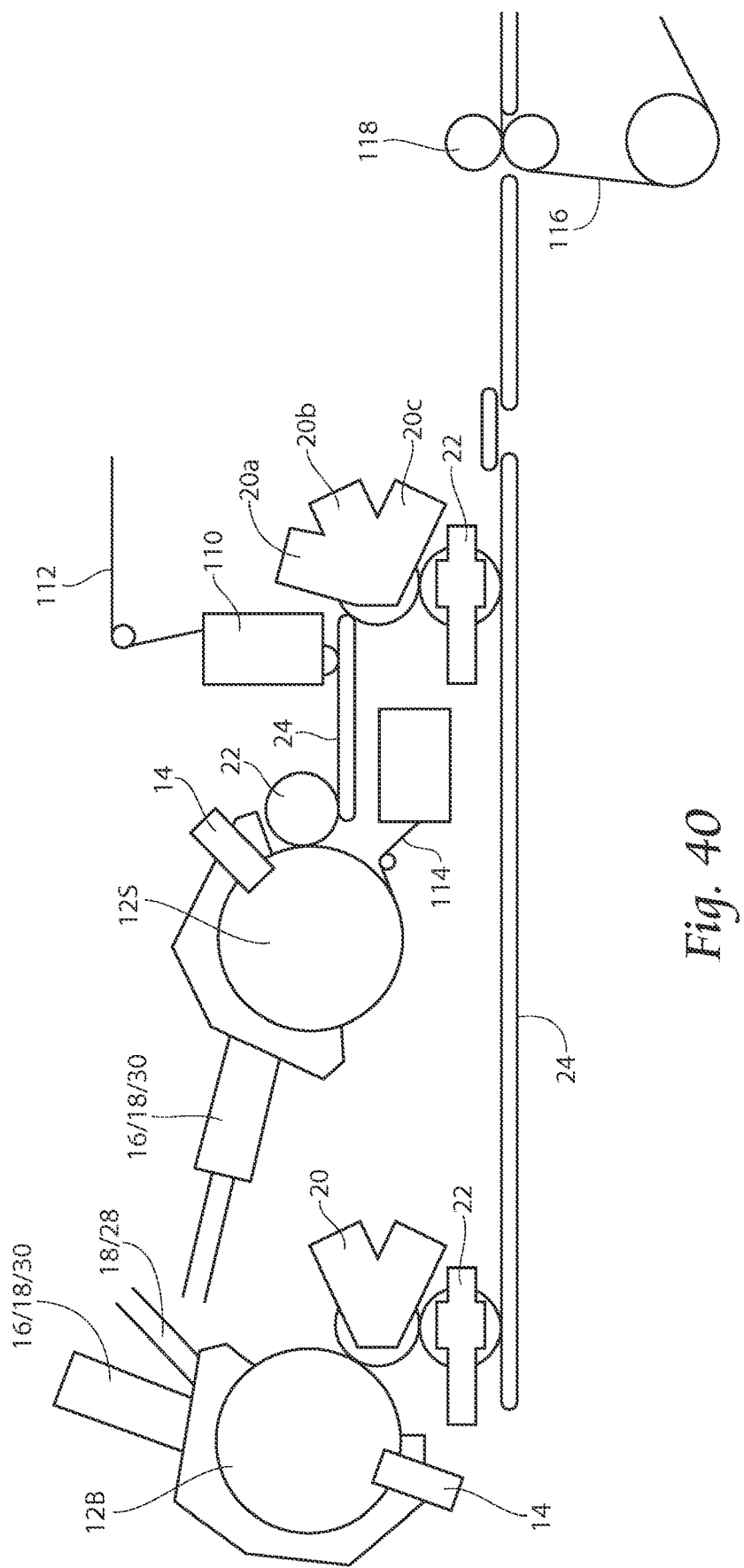

FIG. 40 is a side view of a large and small discrete core forming unit to perform the methods described in FIG. 39. Both of these drums 12S and 12B receive a first layer of dust or fluff/SAP mixture 30 from Fluff/SAP introduction unit 16, onto a pocketed drum 12S or 12B, shown in side view in FIG. 3. The core can be scarfed by scarfing unit 14, which discharges and recycles the scarfed material back into the system through discharge 14D. Next, an additional layer of fluff 28 from fluff introduction unit 18 is applied atop the SAP/Fluff mixture.

The big core forming drum 12B deposits a big core 26B onto a conveyor 24 following debulking unit 20, and after being carried downstream, it receives, after an optional scarfing unit 14, the small core 26S which can be passed through debulking unit 20 and then to a core acceleration unit 22 to match speeds with the big core 26B. Debulking unit 20, as shown in FIG. 40, can comprise a first debulking component 20a, a second embossing unit 20b, and a third core knife station 20c. In this embodiment, the small core 26 is wrapped with a two-piece wrap comprising a first, base tissue 114 fed onto the drum 12S onto which the core 26S is formed. After coming off of the core forming unit 12S and onto conveyor 24, a second, upper tissue 112 is applied to the core 26S by tissue applicator 110, preferably in the manner shown in cross-sectional view in FIG. 41a. The core 26s can be cut on a third station shown schematically at unit 20. The wrapped small core 26S is then deposited on top of the larger, non-wrapped core 26B, and the two cores 26S and 26B are deposited onto incoming poly layer 116, combined by compression unit 118, resulting in a cross-sectional two piece core as shown in FIG. 41a.

Referring to FIGS. 41b and 41c, plan and cross sectional views of an alternative embodiment of the product shown in FIG. 41a, respectively are shown. In this embodiment, a margin 250 is glued, to close the ends of the tissue wrap 114, to create a tea-bag type structure.

Figure 42:
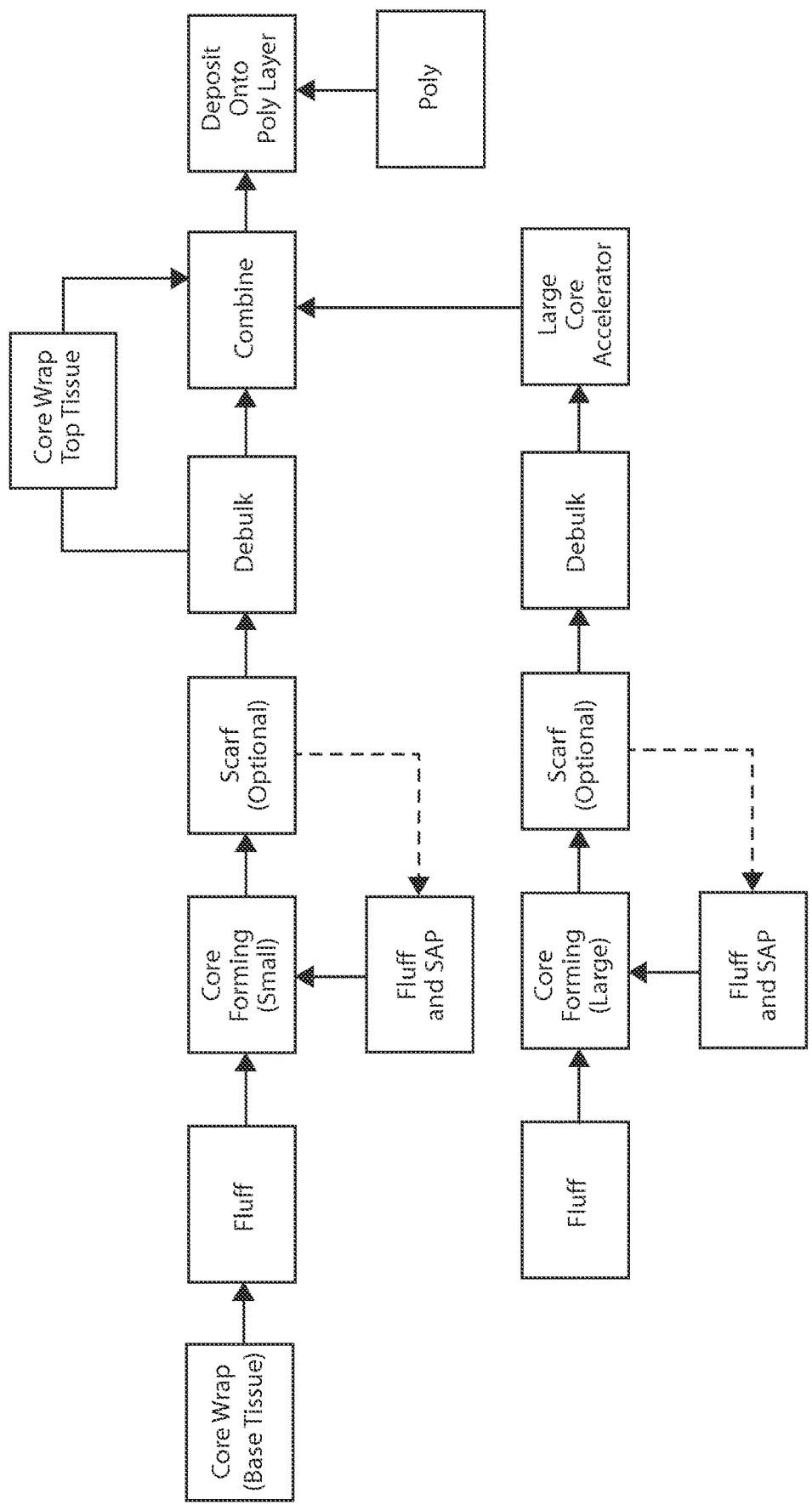
FIGS. 42-44 describe formation of a dual core, with a small, tissue-wrapped core structure laid upon a poly layer, topped by a non-wrapped larger core structure.
Figure 43:
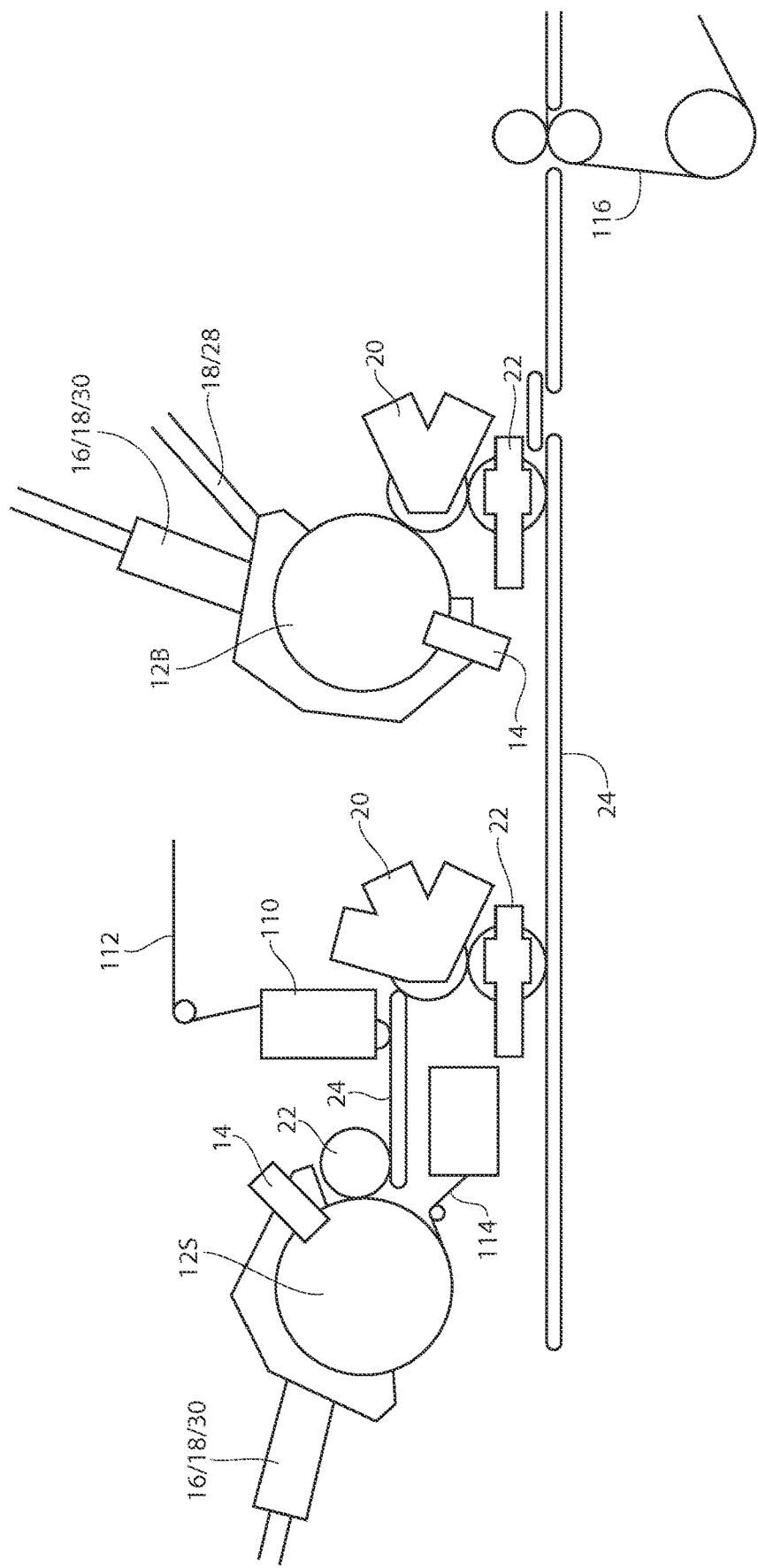
Figure 44:
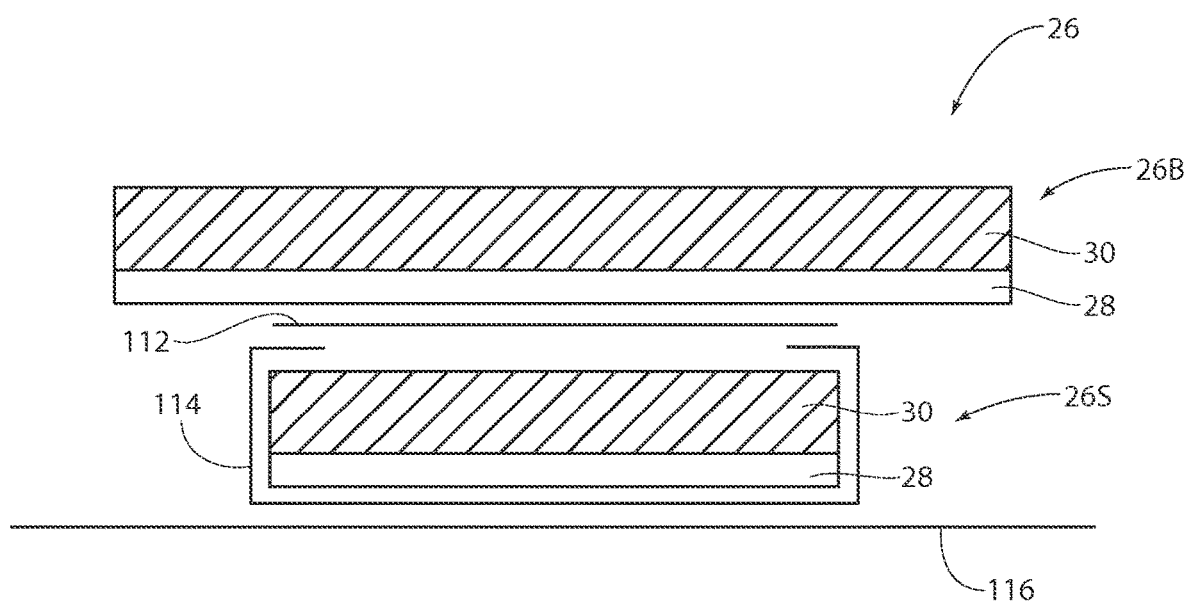

Referring now to FIGS. 42-44, an alternate embodiment of a dual core structure is shown, with a small, tissue-wrapped core structure laid upon a poly layer, topped by a non-wrapped larger core structure.

FIG. 42 is a schematic of machinery to perform this alternate embodiment of the present invention, with a small, tissue-wrapped core structure laid upon a poly layer, topped by a non-wrapped larger core structure, and then passed downstream for further processing.

Referring now to FIG. 43, a side view of a small (wrapped) and large discrete core forming unit to perform the methods described in FIG. 39 is shown. Again, both of the drums 12S and 12B receive a first layer of dust or fluff/SAP mixture 30 from Fluff/SAP introduction unit 16, onto a pocketed drum 12S or 12B, shown in side view in FIG. 3. The core can be scarfed by scarfing unit 14, which discharges and recycles the scarfed material back into the system through discharge 14D. Next, an additional layer of fluff 28 from fluff introduction unit 18 is applied atop the SAP/Fluff mixture.

The small core forming drum 12S deposits a small, wrapped core 26S onto a conveyor 24 following debulking unit 20, and after being carried downstream, it receives, after an optional scarfing unit 14, the small core 26S which can be passed through debulking unit 20 and then to a core acceleration unit 22 to match speeds with the big core 26B.

In this embodiment, the small core 26 is wrapped with a two-piece wrap comprising a first, base tissue 114 fed onto the drum 12S onto which the core 26S is formed. After coming off of the core forming unit 12S and onto conveyor 24, a second, upper tissue 112 is applied to the core 26S by tissue applicator 110, preferably in the manner shown in cross-sectional view in FIG. 43. The large core 26S is then deposited on top of the smaller, wrapped core 26S, and the two cores 26S and 26B are deposited onto incoming poly layer 116, combined by compression unit 118, resulting in a cross-sectional two piece core as shown in FIG. 44.

Figure 45:
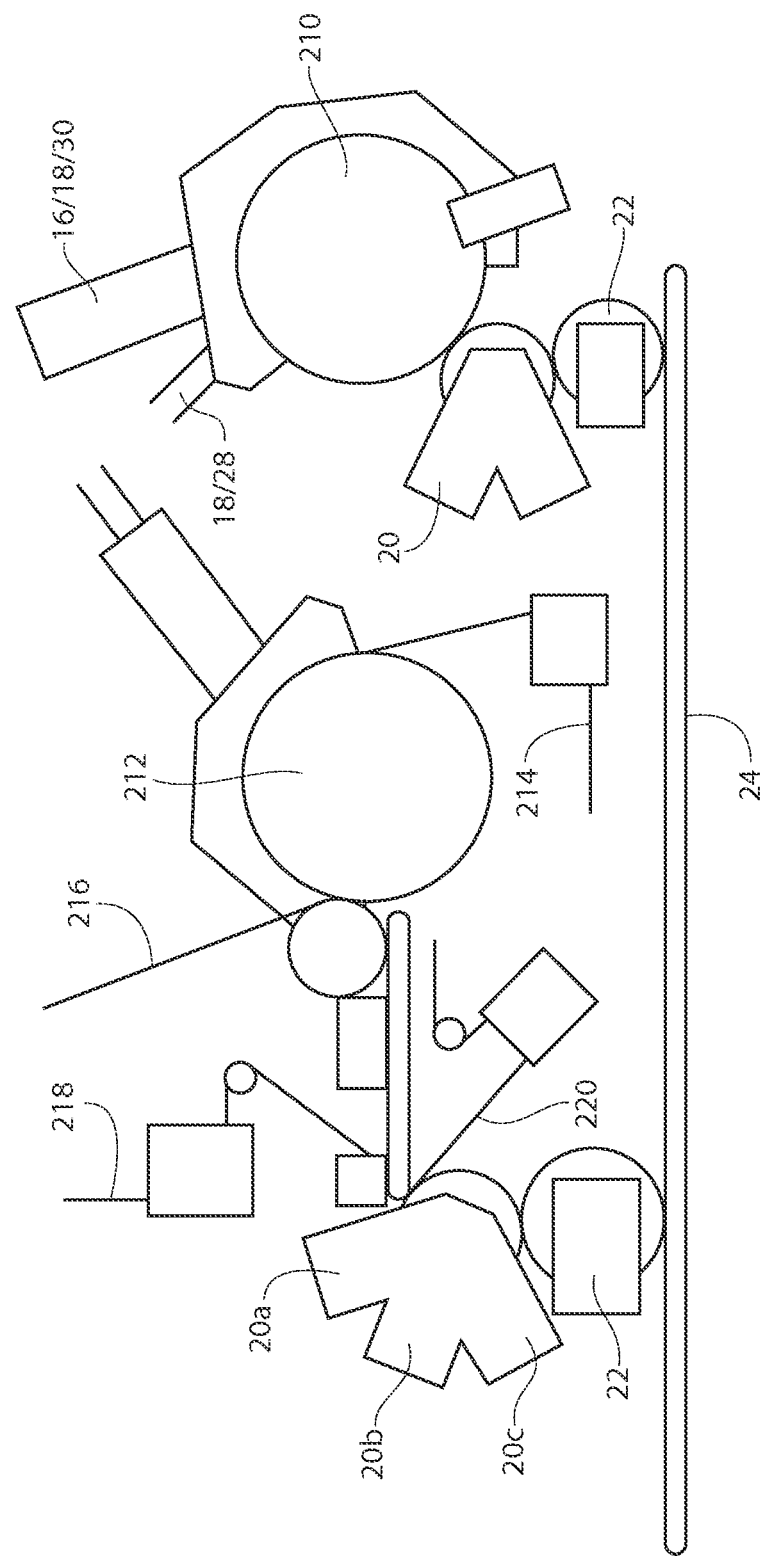
FIG. 45 is a side schematic type view of an alternative embodiment of the present invention, a machine employing pre-made air-laid webs introduced into the core forming process.

Referring now to FIG. 45, a side schematic type view of an alternative embodiment of the present invention, a machine employing pre-made air-laid webs introduced into the core forming process. Pre-made air-laid webs 216, 218, and 220 can be introduced into the core forming process in various configurations, as depicted in FIGS. 46-52.

Referring to FIG. 45, a first, discrete core forming drum 210 is shown, similar to previously described core forming drums. A continuous core forming drum 212 can be provided with a tissue wrap 114 to wrap the formed core. A first debulking component 20a, a second embossing unit 20b, and a third core knife station 20c are together used to process the continuous core prior to placement atop the previously formed discrete core.

Figure 46:
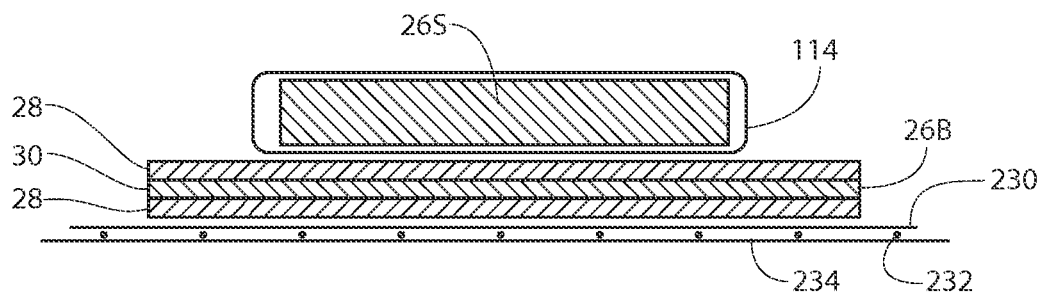
FIGS. 46-52 are side views of various core deposition configurations both with and without introduction of a pre-made air-laid layer in various positions.

Referring to FIGS. 46-52, various core deposition configurations both with and without introduction of a pre-made air-laid layer in various positions are shown. In FIG. 46, small core 26S is wrapped by core wrap 114, and carried by large core 26B, which is carried by poly layer 230 and backsheet 234, which together sandwich crotch elastics 232.

Figure 47:
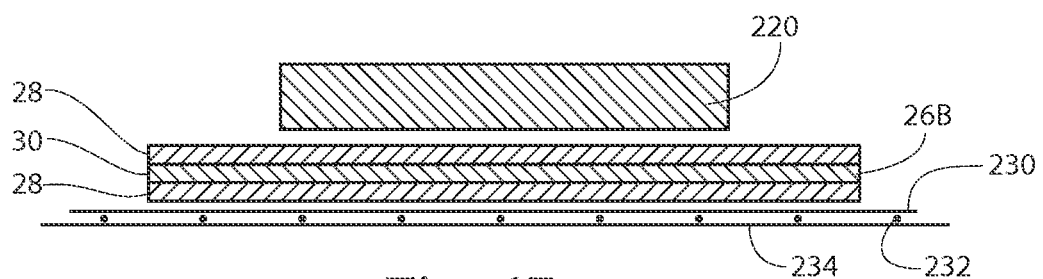

Referring to FIG. 47, a first pre-made air-laid web 220 (provided by the unit shown in FIG. 45) replaces small core 26S, and this web 220 serves as the small core.

Figure 48:
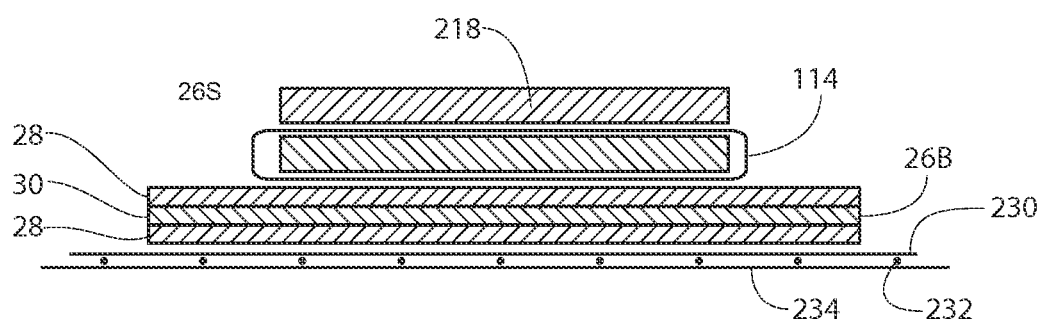

Referring to FIG. 48, a pre-made air-laid layer 218 (provided by the unit shown in FIG. 45) is provided atop a small core 26S wrapped by wrap 114.

Figure 49:
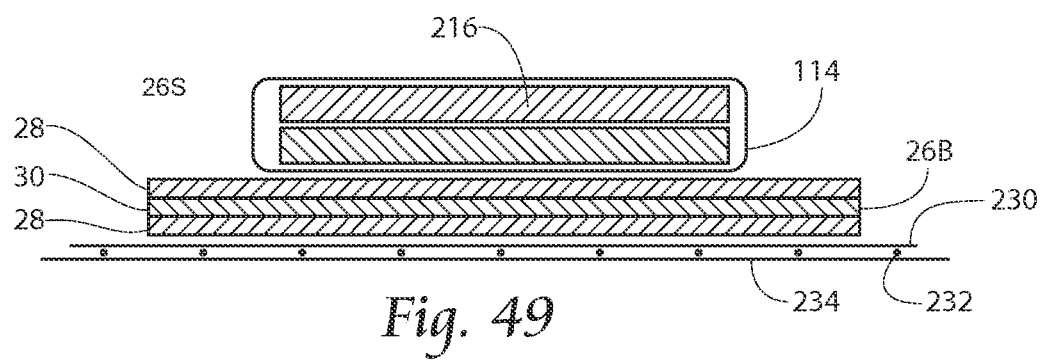

Referring to FIG. 49, both a pre-made air-laid layer 216 (provided by the unit shown in FIG. 45) and small core 26S can be wrapped by wrap 114 and placed atop large core 26B. Small core 26S can comprise either just fluff material 28, or a layered core as described previously.

Figure 50:
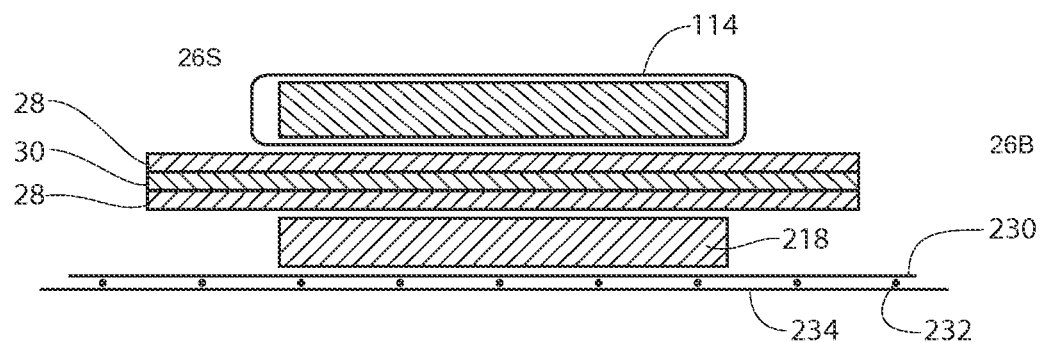

Referring to FIG. 50, small core 26S can be wrapped with tissue 114, carried by core 26B, which can in turn be carried by pre-made air-laid layer 218 (provided by the unit shown in FIG. 45).

Figure 51:
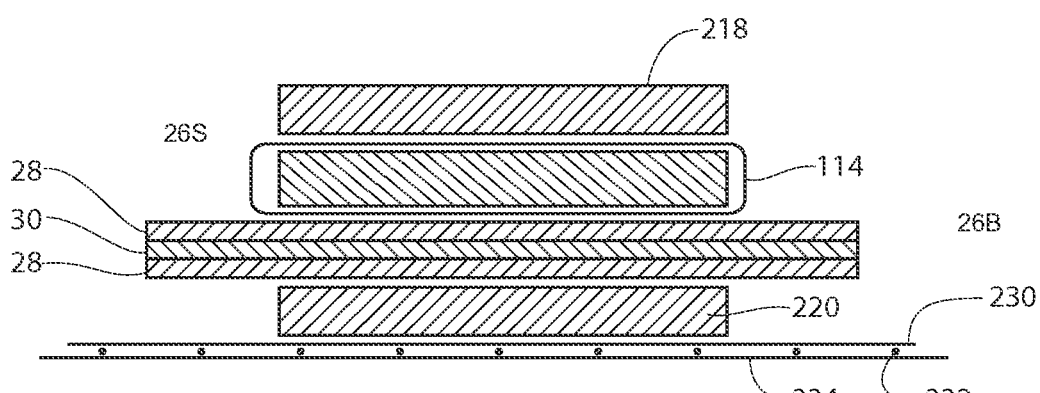

Referring to FIG. 51, pre-made air-laid layer 218 (provided by the unit shown in FIG. 45) can be carried by wrapped small core 26, carried by core 26B, carried by a second pre-made air-laid layer 220 (provided by the unit shown in FIG. 45).

Figure 52:
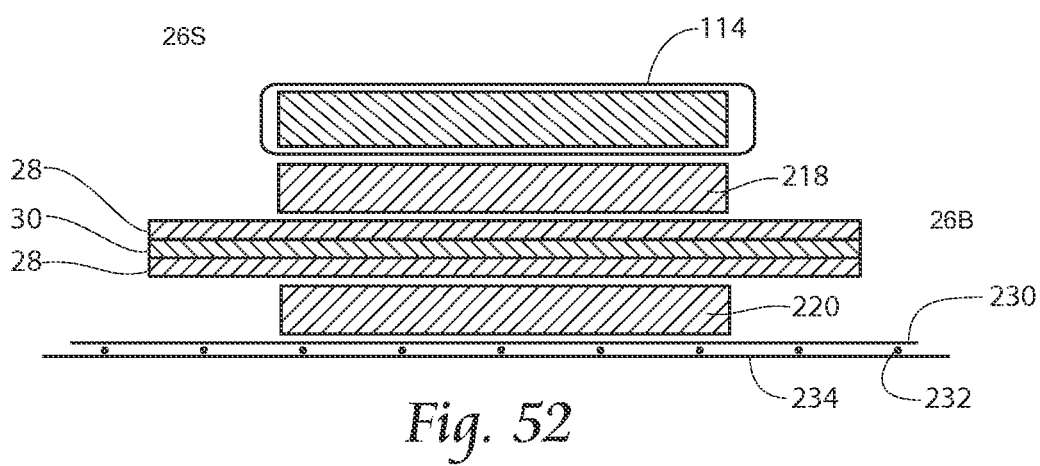

Referring to FIG. 52, wrapped small core 26 can be carried by pre-made air-laid layer 218 (provided by the unit shown in FIG. 45), which can in turn be carried by core 26B, carried by a second pre-made air-laid layer 220 (provided by the unit shown in FIG. 45).

Figure 53:
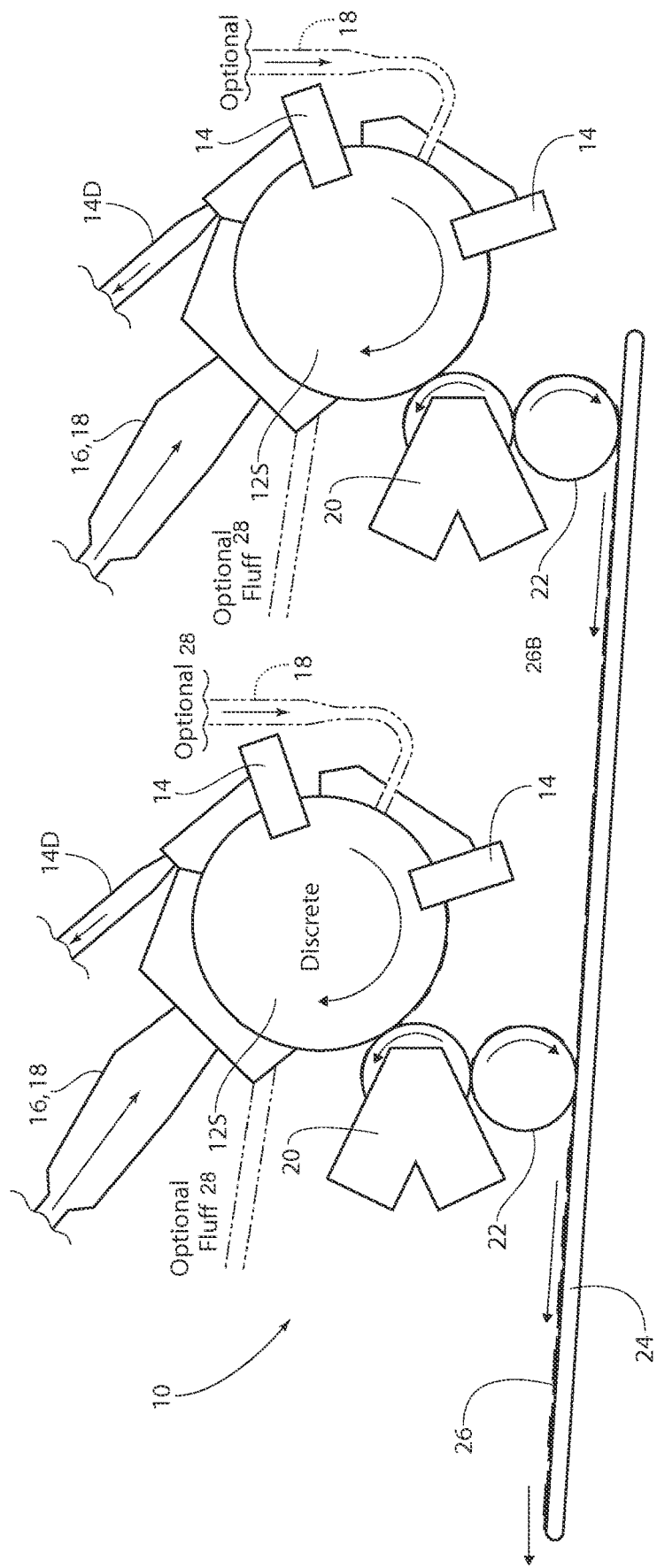
FIG. 53 is a front view of a large and small discrete core forming unit, formed on a screen and combined, and then passed downstream for further processing with optional fluff introduction.
Figure 54:
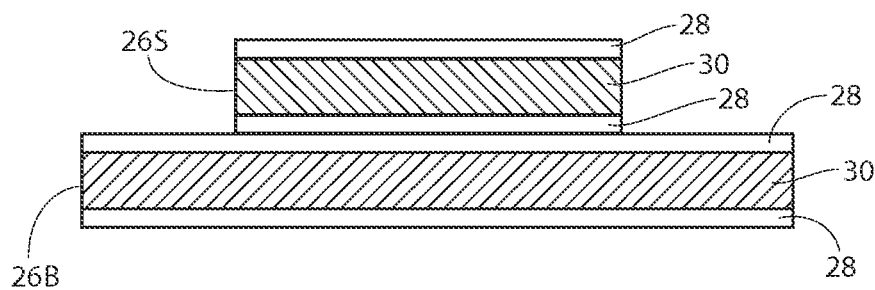
FIG. 54 is a cross-sectional view of a possible strata configuration produced by the machine of FIG. 53.
Figure 55:
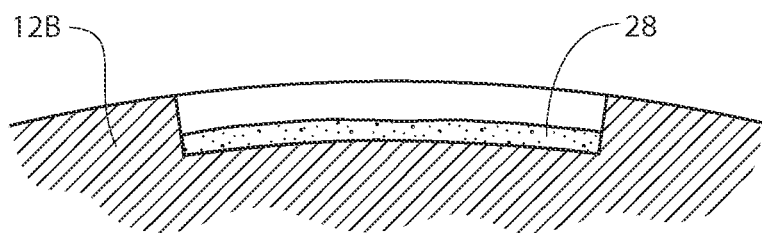
FIGS. 55-60 are side views of an alternate core structure deposition and scarfing operation for creating a first core.
Figure 56:
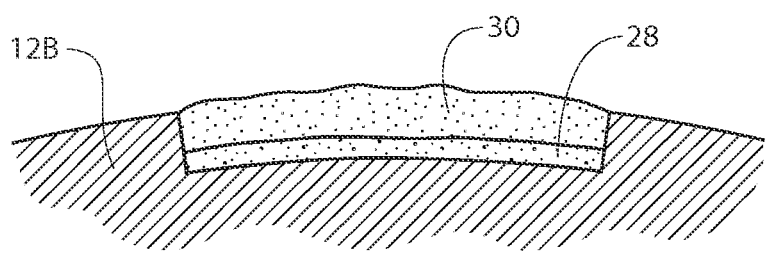
Figure 57:
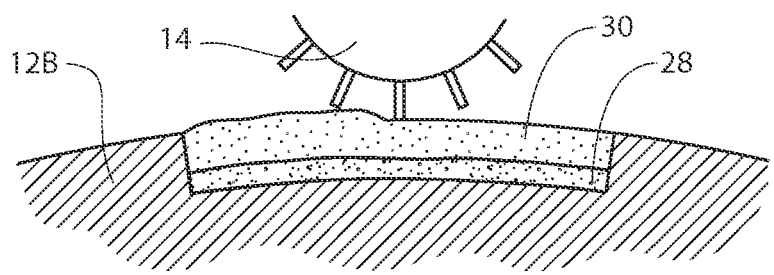
Figure 58:
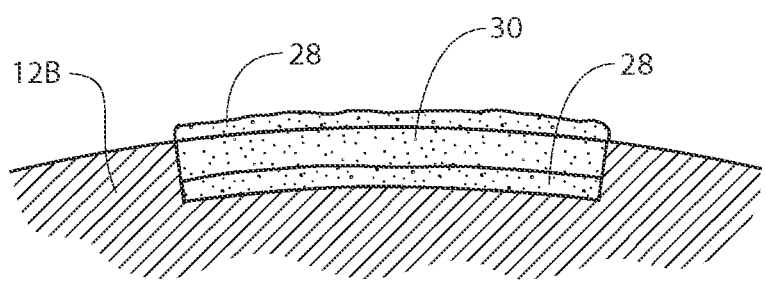
Figure 59:
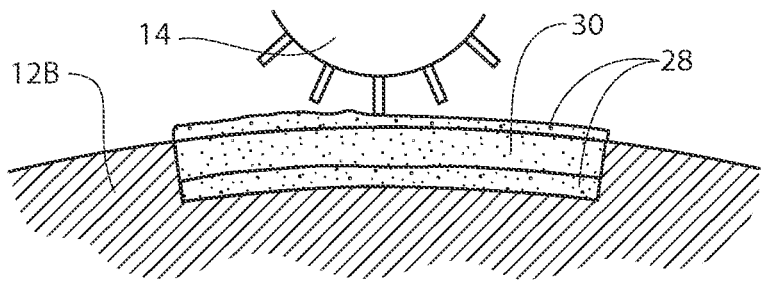
Figure 60:
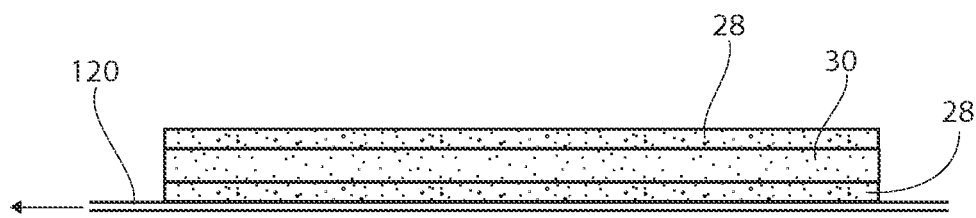
Figure 61:
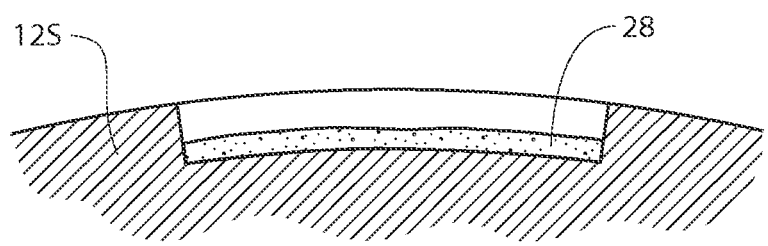
FIGS. 61-66 are side views of an alternate core structure deposition and scarfing operation for creating a second core.
Figure 62:
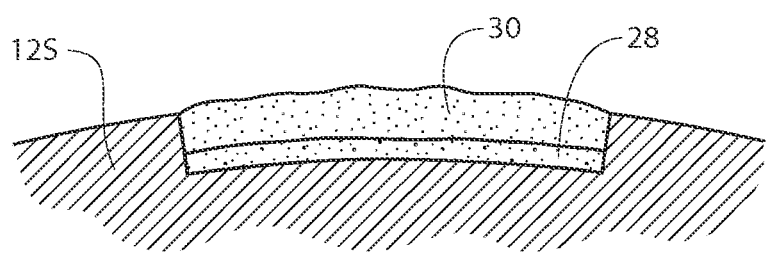
Figure 63:
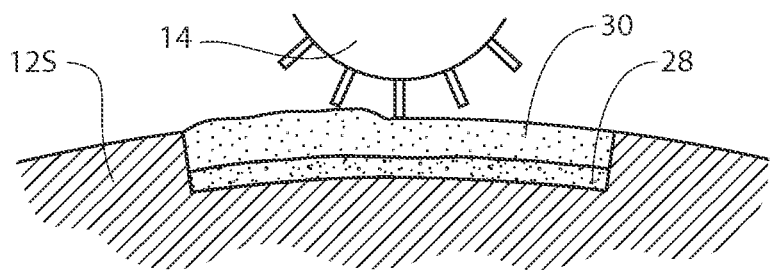
Figure 64:
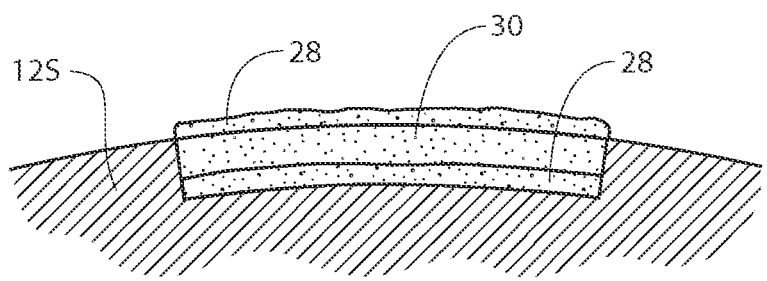
Figure 65:
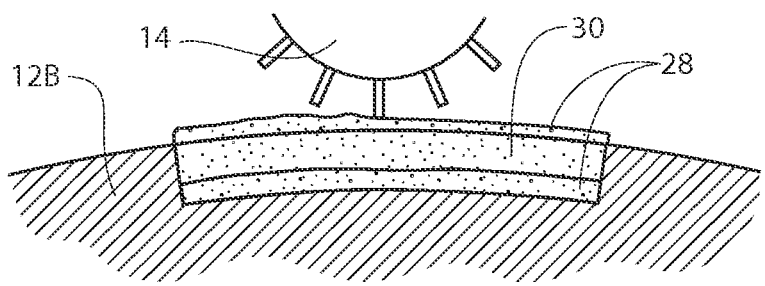
Figure 66:
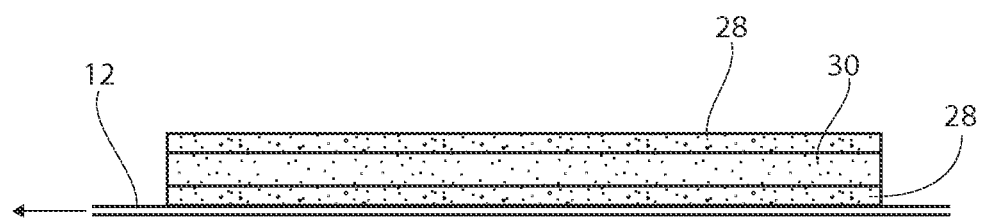

Referring now to FIG. 53 is a front view of a large and small discrete core forming unit similar to that shown in FIG. 2. In this embodiment, additional optional fluff layers 28 can be incorporated to result in cores with cross-sections as shown in FIG. 54.

Referring now to FIGS. 55-60, side views of an alternate core structure deposition and scarfing operation for creating a first core are shown. In this embodiment, a first fluff layer 28 is deposited, next a fluff/SAP mixture 30 is provided and scarfed, and next a second fluff layer 28 is deposited and scarfed, to result in the small core 26S with the configuration shown in FIG. 60 A similar process is shown in FIGS. 61-66 for creating a second core 26B.

Figure 67:
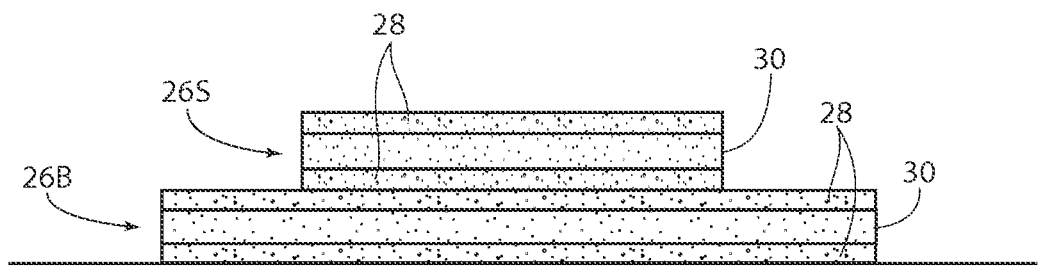
FIGS. 67 and 68 are a cross-sectional and a top view of the placed formed cores of FIGS. 55-66 respectively.
Figure 68:
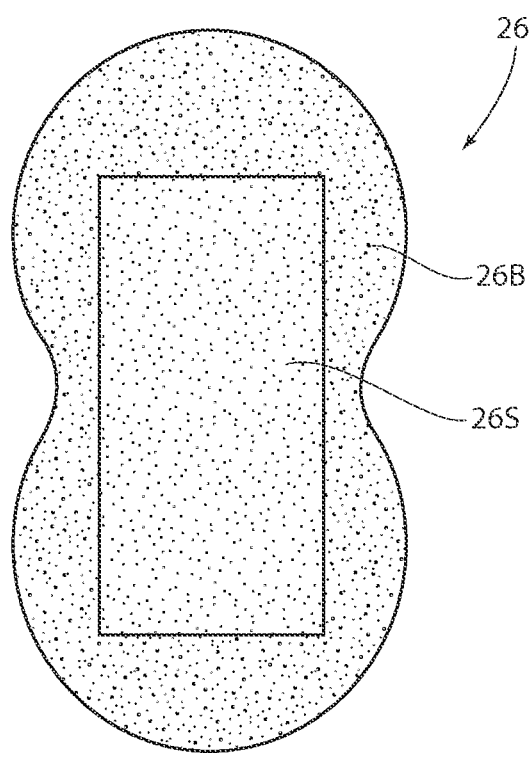

FIGS. 67 and 68 are a cross-sectional and a top view of the placed formed cores 26S and 26B of FIGS. 55-66.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of forming an absorbent core comprising:
   at a first core-forming drum, forming a first core having a first fluff layer and a first super absorbent polymer (SAP) and fluff mixture layer by:
      introducing a non-woven web to the first core-forming drum;
      applying the first fluff layer atop the non-woven web; and
      applying the first SAP and fluff mixture layer atop the first fluff layer;
   at a first debulking unit, debulking said first core;
   at a second core-forming drum, forming a second core having a second SAP and fluff mixture layer;
   at a second debulking unit, debulking said second core;
   after debulking said first core, conveying at a first speed said first core towards said second core-forming drum;
   after debulking said second core, receiving said second core at a second speed at a core acceleration unit, said second speed being less than said first speed;
   wrapping at least one of said first core and said second core with a permeable web;
   with said acceleration unit, accelerating the second core from the second speed to substantially match the first speed; and
   depositing said second core from said core acceleration unit onto said first core.

2. A method according to claim 1, said first core having a contoured figure, and said second core having a substantially rectangular figure, and said second core smaller than said first core.

3. A method according to claim 1, the method further comprising depositing the combined first and second cores onto a top side of a carrier layer traveling at a third speed.

4. A method according to claim 3, wherein said first core is placed onto said carrier layer.

5. A method according to claim 3, wherein said second core is placed onto said carrier layer.

6. A method according to claim 1, the method further comprising introducing a second non-woven web at the second core-forming drum and forming the second core atop the second non-woven web.

7. A method according to claim 3, the method further comprising placing said first core onto said carrier layer, and said second core onto said first core.

8. A method according to claim 3, the method further comprising placing said second core onto said carrier layer, and said first core onto said second core.

9. Previously Presented A method according to claim 1, wherein at least one of said first core and said second core are formed from an air-laid material.

10. A method according to claim 1, wherein said first core is larger than said second core.

11. A method according to claim 1, wherein said second SAP and fluff mixture layer of said second core is placed onto said first, larger core.

12. A method according to claim 1, wherein said first core is formed in a single pocket on a core forming drum.

13. A method according to claim 1, wherein said second core is formed in a single pocket on a core forming drum.

14. A method according to claim 1, wherein at least one of said first and said second cores are formed as a continuous core web, said continuous core web cut by a knife to form discrete cores.

15. A method according claim 1, wherein said second core is formed by severing discrete core pieces from a continuous strip of core material.

16. A method according to claim 1, wherein at least one of said first and said second cores has a width, a length, and at least two different heights.

17. A method according to claim 1, wherein the first and second cores are the same shape.

18. A method according to claim 1, the method further comprising scarfing at least one of the first and second cores.

19. A method according to claim 6, the first core having a first core first end and a first core second end and the second core having a second core first end and a second core second end, the method further comprising sealing at least one of the pair of first core first and second ends and the second core first and second ends.

\* \* \* \* \*